US012226629B2

(12) United States Patent
Dion

(10) Patent No.: US 12,226,629 B2
(45) Date of Patent: Feb. 18, 2025

(54) FORAMINAL LIGAMENT ANCHOR FOR APPLICATION IN DRG THERAPY

(71) Applicant: Advanced Neuromodulation Systems, Inc., Plano, TX (US)

(72) Inventor: Matthew K. Dion, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 18/065,376

(22) Filed: Dec. 13, 2022

(65) Prior Publication Data

US 2023/0116791 A1   Apr. 13, 2023

Related U.S. Application Data

(63) Continuation of application No. 16/864,317, filed on May 1, 2020, now Pat. No. 11,524,155.

(51) Int. Cl.
*A61N 1/05*  (2006.01)

(52) U.S. Cl.
CPC ................... *A61N 1/0558* (2013.01)

(58) Field of Classification Search
CPC ...... A61N 1/0558; A61N 1/057; A61N 1/059; A61N 1/37518
See application file for complete search history.

(56) References Cited

U.S. PATENT DOCUMENTS

| | | | |
|---|---|---|---|
| 8,903,502 B2* | 12/2014 | Perryman | A61N 1/36125 607/72 |
| 9,649,489 B2* | 5/2017 | Wechter | A61N 1/0558 |
| 9,743,918 B2 | 8/2017 | Amplatz et al. | |
| 9,950,159 B2* | 4/2018 | Beck | A61N 1/36167 |
| 10,327,746 B2* | 6/2019 | Glimsdale | A61B 17/12113 |
| 10,449,355 B2* | 10/2019 | Beck | A61N 1/37247 |
| 11,524,155 B2* | 12/2022 | Dion | A61N 1/0558 |
| 2003/0199961 A1* | 10/2003 | Bjorklund | A61N 1/057 607/126 |
| 2007/0255295 A1* | 11/2007 | Starkebaum | A61N 1/05 607/149 |
| 2009/0018606 A1* | 1/2009 | Sparks | A61N 1/0517 607/40 |
| 2012/0035692 A1* | 2/2012 | Cantlon | A61N 1/0558 607/116 |

(Continued)

*Primary Examiner* — Eric D. Bertram
(74) *Attorney, Agent, or Firm* — Fogarty LLP

(57) ABSTRACT

In one embodiment, a system for stimulating the dorsal root ganglion of a patient comprises an elongate flexible implantable stimulation lead adapted to apply the stimulation pulses to the dorsal root ganglion of the patient, wherein the distal end comprises at least one electrode. A first segment and a second segment of the anchor are configured to transition between a collapsed configuration and deployed configuration. A central channel in the first segment and the second segment allows the anchor to be advanced along the stimulation lead from a proximal end toward the distal end while in the collapsed configuration. The central channel of each segment grips onto the stimulation lead in the deployed configuration so that the segment does not move from a deployed position on the stimulation lead. The first segment and the second segment may be deployed on opposite sides of foraminal ligament to anchor the stimulation lead.

19 Claims, 18 Drawing Sheets

(56) References Cited

U.S. PATENT DOCUMENTS

| | | | |
|---|---|---|---|
| 2013/0310901 A1* | 11/2013 | Perryman | A61N 1/025 607/117 |
| 2014/0018884 A1* | 1/2014 | Leven | A61N 1/0558 607/116 |
| 2014/0155936 A1* | 6/2014 | Lee | A61N 1/0558 606/232 |
| 2014/0155973 A1* | 6/2014 | Grigsby | A61N 1/0558 607/116 |
| 2014/0330287 A1* | 11/2014 | Thompson-Nauman | A61N 1/05 607/116 |
| 2015/0251004 A1 | 9/2015 | Imran et al. | |
| 2015/0297882 A1* | 10/2015 | Barker | A61N 1/0558 607/116 |
| 2015/0342635 A1* | 12/2015 | Tsamir | A61B 17/3476 604/164.04 |
| 2016/0310732 A1* | 10/2016 | Beck | A61N 1/36167 |
| 2017/0136232 A1 | 5/2017 | Oron et al. | |
| 2017/0165478 A1* | 6/2017 | Racz | A61M 31/00 |
| 2018/0110974 A1* | 4/2018 | Deer | A61N 1/0553 |
| 2018/0169405 A1* | 6/2018 | Kent | A61N 1/36071 |
| 2018/0221659 A1* | 8/2018 | Beck | A61N 1/36067 |
| 2018/0272125 A1* | 9/2018 | Sandhu | A61N 1/0558 |
| 2018/0311494 A1* | 11/2018 | Wang | A61N 1/0529 |
| 2019/0110811 A1* | 4/2019 | Racz | A61N 1/057 |
| 2019/0142431 A1* | 5/2019 | Liu | A61B 17/12122 606/213 |
| 2019/0336779 A1* | 11/2019 | Nelson | A61N 1/3956 |
| 2020/0046972 A1* | 2/2020 | Beck | A61N 1/36167 |
| 2022/0176133 A1* | 6/2022 | Buddha | A61N 1/37235 |

* cited by examiner

FORAMINAL LIGAMENT ANCHOR FOR APPLICATION IN DRG THERAPY

CROSS-REFERENCE TO RELATED APPLICATION

This is a continuation of, and claims benefit of, U.S. patent application Ser. No. 16/864,317, filed May 1, 2020, and issued as U.S. Pat. No. 11,524,155, which is hereby incorporated herein by reference in its entirety.

BACKGROUND

In 1959, neurosurgeon Willem Noordenbos reported that a signal carried along large diameter fibers may inhibit the signal carried by the thinner pain fibers. From this, Melzack and Wall proposed the "gate control" theory of pain. The gate control theory postulates that stimulation of large myelinated fibers suppresses the response of dorsal horn neurons to input from small, unmyelinated peripheral pain fibers. The gate control theory provided the theoretical foundation for the use of spinal cord stimulation (SCS) as a clinical treatment for chronic pain. The first experimental clinical use of SCS was shortly followed by clinical trials of SCS in patients suffering from intractable chronic pain in the early seventies.

In conventional SCS, an electrode is positioned over the spinal cord and connected to an internal pulse generator. All pulse generators currently available deliver tonic pulses that can be modified by altering the pulse width, frequency, and amplitude to get maximal pain suppression. The internal pulse generators can use either constant voltage or constant current to modulate the underlying cells or networks. Electrical stimulation of large afferents of the dorsal column by an electrode placed dorsomedially in the epidural space elicits a tingling sensation (paresthesia) in the corresponding dermatomes. To obtain successful treatment of chronic neuropathic pain by conventional SCS, the stimulation-induced paresthesia must cover the pain area completely.

As illustrated in FIG. 1, prior art spinal column or spinal cord stimulators (SCS) commonly deliver electrical energy to the spinal cord through an elongate paddle 101 or epidural electrode array containing electrodes 102 positioned external to the spinal cord dura layer 103. The spinal cord dura layer 103 surrounds the spinal cord 104 and is filled with cerebral spinal fluid (CSF). The spinal cord 104 is a continuous body and three spinal levels 105 of the spinal cord 104 are illustrated. For purposes of illustration, spinal levels 105 are sub-sections of the spinal cord 104 depicting that portion where the dorsal and ventral roots join the spinal cord 104. The peripheral nerve 106 divides into the dorsal root 107 and dorsal root ganglion (DRG) 108 and the ventral nerve root 109 each of which feed into the spinal cord 104. An ascending pathway 110 is illustrated between level 2 and level 1 and a descending pathway 111 is illustrated from level 2 to level 3. Spinal levels 105 can correspond to the vertebral levels of the spine commonly used to describe the vertebral bodies of the spine. For simplicity, each level illustrates the nerves of only one side and a normal anatomical configuration would have similar nerves illustrated in the side of the spinal cord 104 directly adjacent the paddle 101.

Typically, SCS are placed in the spinal epidural space. For example, the paddle 101 is about 8 mm wide and from 24 to 60 mm long depending upon how many spinal levels are stimulated. The illustrated electrode paddle 101 is adapted to conventionally stimulate 112 all three spinal levels 105. These exemplary levels 1, 2 and 3 could be anywhere along the spinal cord 104. Positioning a stimulation paddle 101 in this manner results in the electrodes 102 spanning a plurality of nerves, here the DRG 108, the ventral root 109 and peripheral nerve 106 on multiple spinal levels More recent SCS therapies have been applied to address chronic pain in patients. One example is BurstDR™ stimulation (available in SCS systems of Abbott, Plano TX). This type of SCS has been reported to address chronic pain in patients without necessarily inducing paresthesia in patients. De Ridder D, Vanneste S, Plazier M, van der Loo E, Menovsky T., Burst Spinal Cord Stimulation: Toward Paresthesia-Free Pain Suppression, Neurosurgery 2010; 66:986-90.

The DRG is a neural structure located at each segmental level of the spinal column in the lateral epidural space within the spinal foramen. the DRG contains the cell bodies of the primary sensory neurons. The DRG is involved in the transduction of pain to the central nervous system. It has been experimentally shown that electrical stimulation of the DRG reduces the excitability of the DRG neurons. It has been reported that incoming afferent pain signals spread over the different levels of the spinal cord and dorsal root ganglia and as a consequence communication between the segmental levels takes effect. The possible advantages of DRG stimulation include an improved ability to achieve pain relief in locations that are typically challenging to effectively achieve with SCS and enhanced stability of the stimulation regardless of body position. However, current deployment of the electrode leads is subject to migration, which is a threat to implant longevity and can result in therapy loss.

SUMMARY

The present invention provides devices, systems, and methods for stimulation of tissues and structures within a body of a patient. In particular, implantable leads are provided which are flexible, reliable, and easily manufacturable for a variety of medical applications. Such leads are particularly suitable for stimulation of the spinal anatomy, more particularly suitable for stimulation of specific nerve anatomies, such as the dorsal root (optionally including the dorsal root ganglion). Such stimulation is enhanced by anchoring the leads close to the target treatment area.

In an example embodiment, a system for stimulating the dorsal root ganglion of a patient comprises an elongatable, flexible, implantable stimulation lead comprising a proximal end adapted to receive stimulation pulses from an implantable pulse generator and a distal end adapted to apply the stimulation pulses to the dorsal root ganglion of the patient, wherein the distal end comprises at least one electrode. The system further comprises an anchor having a first segment and a second segment, wherein each segment is configured to transition between a collapsed configuration and deployed configuration. The first segment and the second segment each have a central channel that is configured to surround the stimulation lead. The central channel is configured to allow the anchor to be advanced along the stimulation lead from the proximal end toward the distal end while in the collapsed configuration. The central channel of each segment is configured to grip onto the stimulation lead when the segment is in the deployed configuration so that the segment does not move from a deployed position on the stimulation lead.

The first segment and the second segment are configured to independently transition from the collapsed configuration and the expanded configuration. A connector may be attached between the first segment and the second segment to keep the first segment and the second segment in a spaced relationship.

The first segment and the second segment are configured to be deployed on opposite sides of an anatomical structure with the first segment on the distal side of the structure and the second segment on the proximal side of the structure. The anatomical structure may be a foraminal ligament. The deployed configuration for the first segment and the second segment may be a disk shape.

The first segment and the second segment may each comprise a layer of tubular metal fabric having a plurality of braided metal strands, the tubular metal fabric having a preset expanded configuration corresponding to the deployed configuration.

An implantable pulse generator may be configured to provide electrical stimulation to a target dorsal root ganglion using one or more electrodes of the stimulation lead.

In another example embodiment, a method of anchoring a stimulation lead for a dorsal root ganglion (DRG) of a patient comprises advancing the stimulation lead through an opening in a ligament in the patient's foramen; positioning the stimulation lead so that one or more electrodes of the stimulation lead are adjacent to a target DRG; advancing a first portion of an anchor device along the stimulation lead and through the opening in the ligament while the first portion is in a collapsed configuration; and when the first portion of the anchor device is on a distal side of the ligament, allowing the first portion to expand to a deployed configuration, wherein the first portion locks or grips onto the stimulation lead in the deployed configuration. In the deployed configuration, the first portion of the anchor device comprises a size that is too large to pass through the opening in the ligament.

The method may further comprise advancing a second portion of the anchor device along the stimulation lead while the second portion is in a collapsed configuration; and when the second portion of the anchor device abuts a proximal side of the ligament, allowing the second portion to expand to a deployed configuration, wherein the second portion locks onto the stimulation lead in the deployed configuration.

The first portion and the second portion of the anchor device may be coupled by a central connector. Alternatively, the first portion and the second portion of the anchor device may be separate components that are advanced along the stimulation lead independently.

The first portion of the anchor device has a central opening that closes in the deployed configuration to lock onto the stimulation lead. The deployed configuration for the first portion of the anchor device may be a disk shape. The first portion of the anchor device may comprise a layer of tubular metal fabric having a plurality of braided metal strands, the tubular metal fabric having a preset expanded configuration corresponding to the deployed configuration.

The method may further comprise providing electrical stimulation to the target DRG using one or more electrodes of the stimulation lead.

The method may further comprise suturing the stimulation lead to fascia or an interspinous ligament.

DETAILED DESCRIPTION

A foraminal anchor for a DRG stimulation lead is disclosed herein. The anchor may be delivered percutaneously or via a surgical or open technique. The anchor is collapsible and has a hole that allows for the passage of the lead when it is not deployed, but the hole decreases diameter when the anchor is deployed to grab onto the lead. When deployed, the anchor expands and grabs onto both sides of a foraminal ligament. The anchor reduces the likelihood of stimulation electrode movement and/or lead migration because the anchor holds the lead in place at a location near the target DRG stimulation area. The anchor may be built into the stimulation lead delivery tool design so that the anchor can detach from the delivery tool when desired. Alternatively, the anchor may be a standalone component of the DRG system. By leveraging the foraminal ligaments, the anchor does not require any suturing, thereby reducing complexity in cases where clinicians are not comfortable with suturing in small workspaces.

Figure 1:
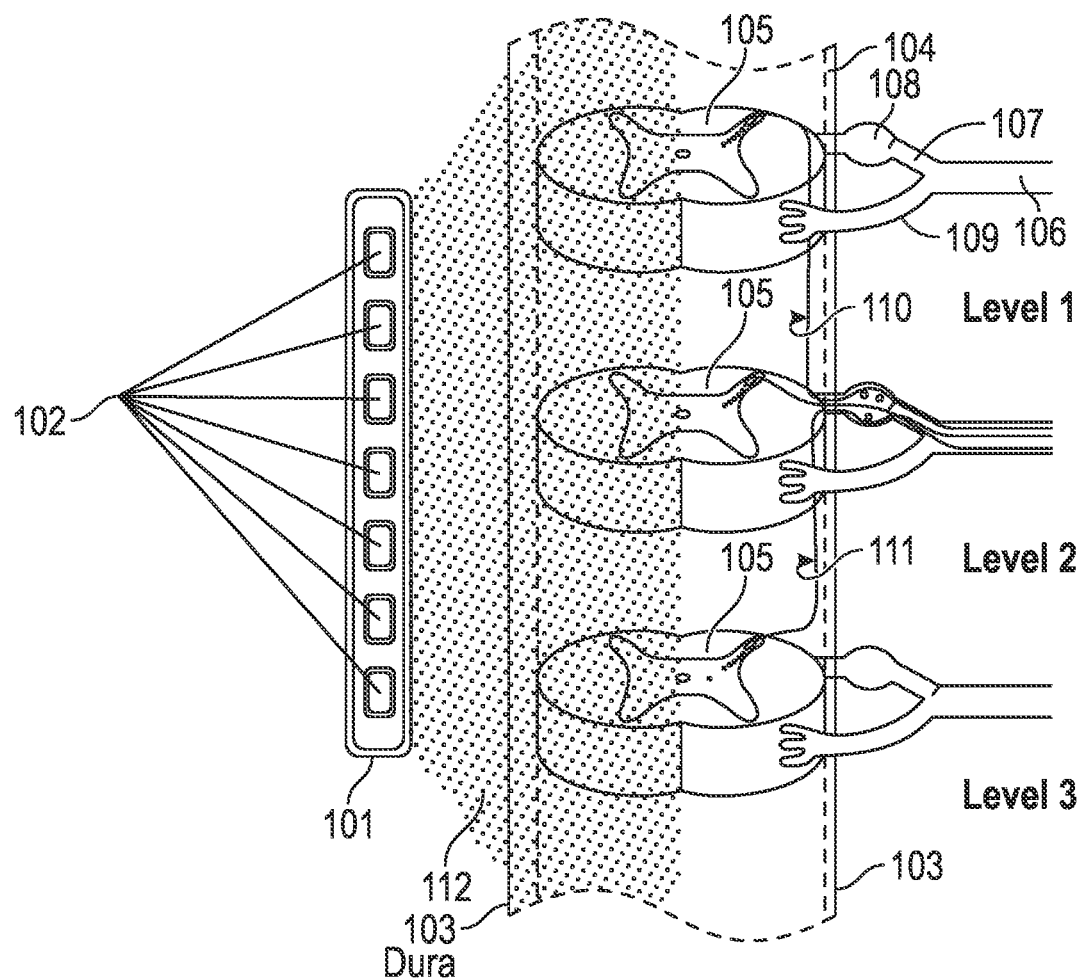
FIG. 1 illustrates a conventional epidural electrode array positioned external to and stimulating a portion of the spinal cord.
Figure 2A:
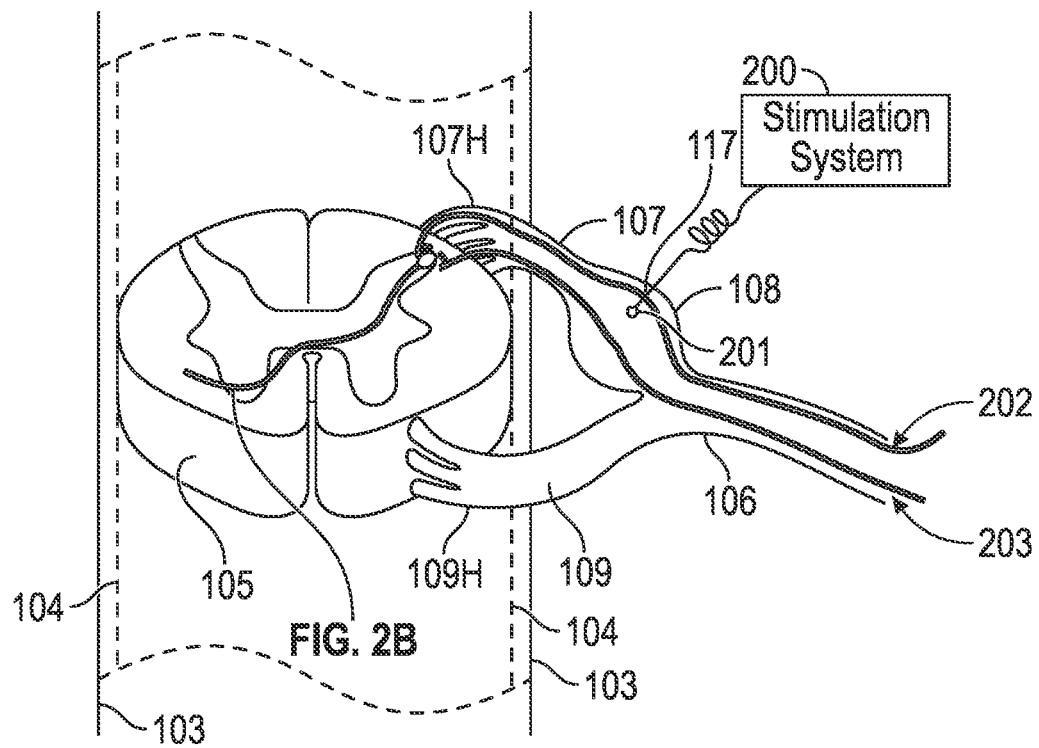
FIG. 2A illustrates an embodiment an electrode implanted into a spinal dorsal root ganglion (DRG).

FIG. 2A illustrates an embodiment of a stimulation system 200 of the present invention in place with an electrode 201 implanted into a spinal DRG 108. For purposes of illustration, spinal level 105, a sub-section of the spinal cord 104, is used to depict where the dorsal root 107 and ventral root 109 join the spinal cord 104, indicated by 107H and 109H respectively. The peripheral nerve 106 divides into the dorsal root 107 and DRG 108 and the ventral nerve root 109. For simplicity, the nerves of only one side are illustrated and a normal anatomical configuration would have similar nerves positioned on the other side. The spinal dura layer 103 surrounds the spinal cord 104 and is filled with cerebral spinal fluid (CSF). For clarity, the spinal dura layer or dura mater 103 alone is used to represent the three spinal meninges—the pia mater, the arachnoid mater and the dura mater—that surround and protect the spinal cord 104.

Note that the electrode 201 is implanted medial to the peripheral nerve 106 after the nerve root splits into the ventral nerve 109 containing the motor nerves and the dorsal root 107 containing the sensory nerves. The electrode 201 is also implanted lateral of the dura layer 103. The advantageous placement of one or more electrode embodiments of the present invention enables selective stimulation of neural tissue, such as a nerve root ganglion, without stimulation of surrounding neural tissue. In this example, a DRG 108 is stimulated with little or imperceptible amounts of stimulation energy provided to the motor nerves within the ventral nerve root 106, portions of the spinal cord 104, spinal level 105, or the peripheral nerve 106. Embodiments of the present invention are particularly well suited for providing pain control since the sensory fibers running through the DRG 108 may be specifically targeted. Advantageously, embodiments of the present invention may neuromodulate one or more the dorsal root ganglia for pain control without influencing surrounding tissue.

Figure 2B:
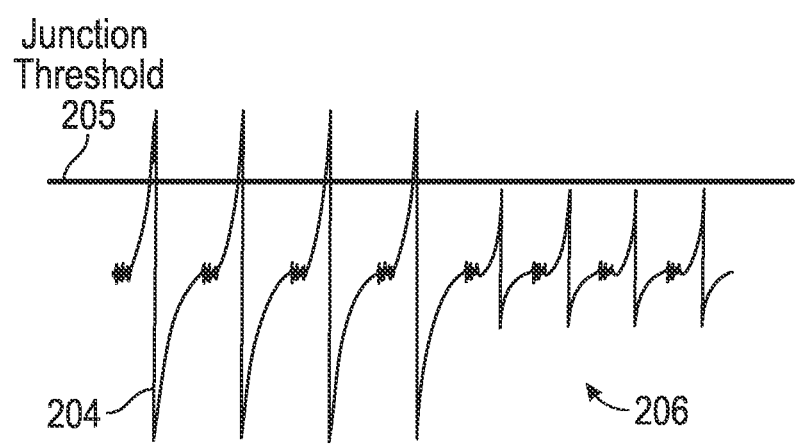
FIG. 2B illustrates how selective stimulation techniques of FIG. 2A may raise a response threshold.

The stimulation system 200 includes a pulse generator that provides stimulation energy in programmable patterns adapted for direct stimulation of neural tissue using small area, high impedance microelectrodes. The level of stimulation provided is selected to preferentially stimulate the Aβ and Aα fibers 202 over the c-fibers 203. Stimulation energy levels used by embodiments of the present invention utilize lower stimulation energy levels than conventional non-direct, non-specific stimulations systems because the electrode 201 is advantageously placed on, in or about a DRG 108. Based on conventional gate control theory, it is believed that, by stimulating the faster transmitting Aβ and Aα fibers 202 using the stimulation methods of the present invention, the signal 204 (FIG. 2B) from the fibers 202 will release opiates at the junction of the dorsal root 107 and the spinal cord 104. This release raises the response threshold at that junction (elevated junction threshold 205). The later arriving c-fiber signal 206 remains below the elevated junction threshold 205 and goes undetected.

Accordingly, some embodiments of the present invention provide selective stimulation of the spinal cord, peripheral nervous system, and/or one or more dorsal root ganglia. As used herein, in one embodiment, selective stimulation means that the stimulation substantially only neuromodulates or neurostimulates a nerve root ganglion. In one embodiment, selective stimulation of a DRG 108 leaves the motor nerves unstimulated or unmodulated. In addition, in other embodiments, selective stimulation can also mean that within the nerve sheath, the A-myelinated fibers are preferentially stimulated or neuromodulated as compared to the c-unmyelinated fibers. As such, embodiments of the present invention advantageously utilize the fact that A-fibers carry neural impulses more rapidly (almost twice as fast) as c-fibers. Some embodiments of the present invention are adapted to provide stimulation levels intended to preferentially stimulate A-fibers over c-fibers.

In additional embodiments, selective stimulation can also mean that the electrode is in intimate contact with the tissue or other nervous system component that is the subject of stimulation. This aspect recognizes our advantageous use of electrode placement. In various embodiments, one or more stimulation electrodes are placed (1) against or in contact with the outer sheath of a nerve root ganglion; (2) within a nerve root ganglion; (3) within the root ganglion interfascicular space; (4) in contact with a portion of the spinal cord; (5) in a position that requires piercing of the epidural space, the dura, nerve root epineurium or a portion of the spinal cord; (6) in contact with a portion of the sympathetic nervous system or (7) in contact with neural tissue targeted for direct stimulation.

Moreover, selective stimulation or neuromodulation concepts described herein may be applied in a number of different configurations. Unilateral (on or in one root ganglion on a level), bilateral (on or in two root ganglion on the same level), unilevel (one or more root ganglion on the same level) or multi-level (at least one root ganglion is stimulated on each of two or more levels) or combinations of the above including stimulation of a portion of the sympathetic nervous system and one or more dorsal root ganglia associated with the neural activity or transmission of that portion of the sympathetic nervous system. As such, embodiments of the present invention may be used to create a wide variety of stimulation control schemes, individually or overlapping, to create and provide zones of treatment.

Figure 3A:
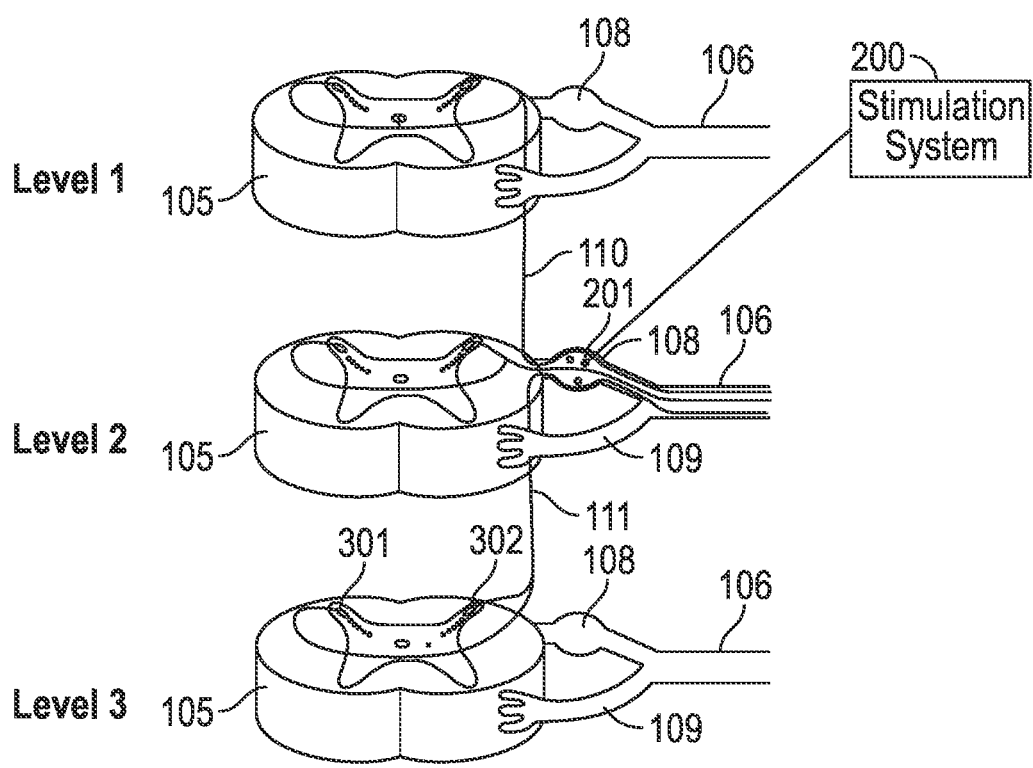
FIG. 3A illustrates a stimulation system with an electrode embodiment of the present invention implanted into a DRG of a spinal level.

FIG. 3A illustrates an embodiment of a stimulation system 200 of the present invention with an electrode 201 implanted into a DRG 108. The figure illustrates three representative spinal levels 105 (i.e., spinal levels 1-3) of the spinal cord 104. The peripheral nerve 106 feeds into the DRG 108 and the ventral nerve root 109 each of which feed into the spinal cord 104. The dorsal horns 301, 302 are also indicated. For clarity, the dura 103 and complete spinal cord 104 are not illustrated but are present as described elsewhere in this application and as occur in human anatomy. These exemplary levels 1, 2 and 3 could be anywhere along the spinal cord 104. For simplicity, each level illustrates the nerves of only one side.

Using level 2 as a reference, an ascending pathway 110 is illustrated between level 2 and level 1 and a descending pathway 111 is illustrated from level 2 to level 3. Application of stimulation energy or signals to the DRG 108 in level 2 may be used to block signals progressing upstream from level 2 towards the path/pathways 110. Moreover, modulation applied to portions of level 2 but may also be used to effectively block the neuron paths/pathways from another level (here, alternatively using levels 1 and/or 3) from reaching the brain. As such, application of stimulation to the level 2 DRG 108 using an embodiment of an apparatus and/or method of the present invention may advantageously provide an effective block of intrasegment pain pathways as well. It is to be appreciated that while three continuous levels are illustrated, some embodiments of the present invention may be used to stimulate two or more adjacent levels and still other embodiments may be used to stimulate two or more non-adjacent levels, or combinations thereof.

Figure 3B:
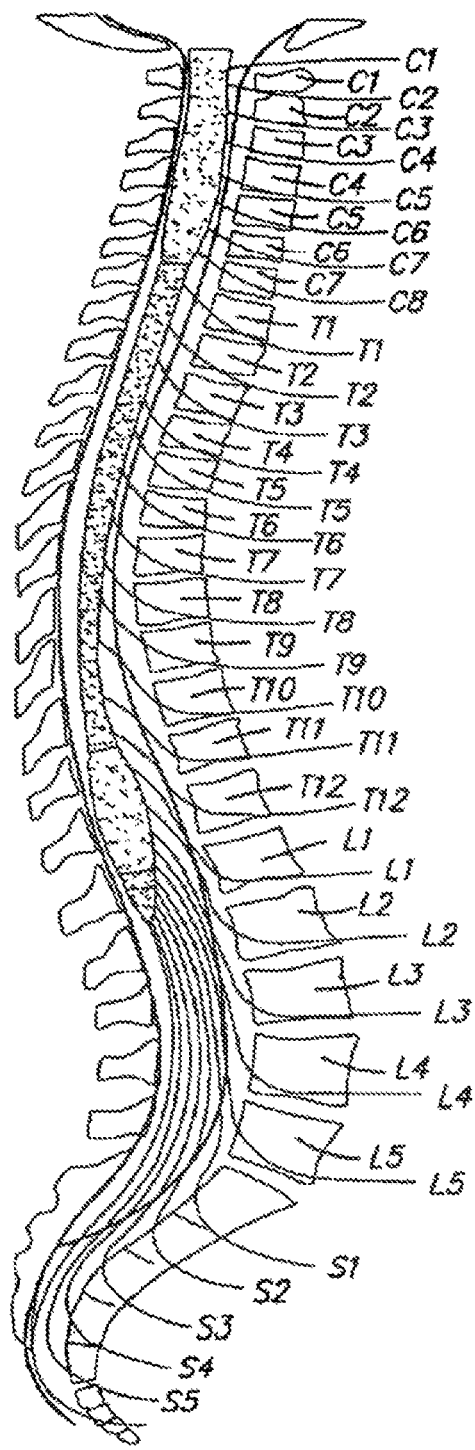
FIG. 3B relates the spinal nerve roots to their respective vertebral spinal levels.
Figure 3C:
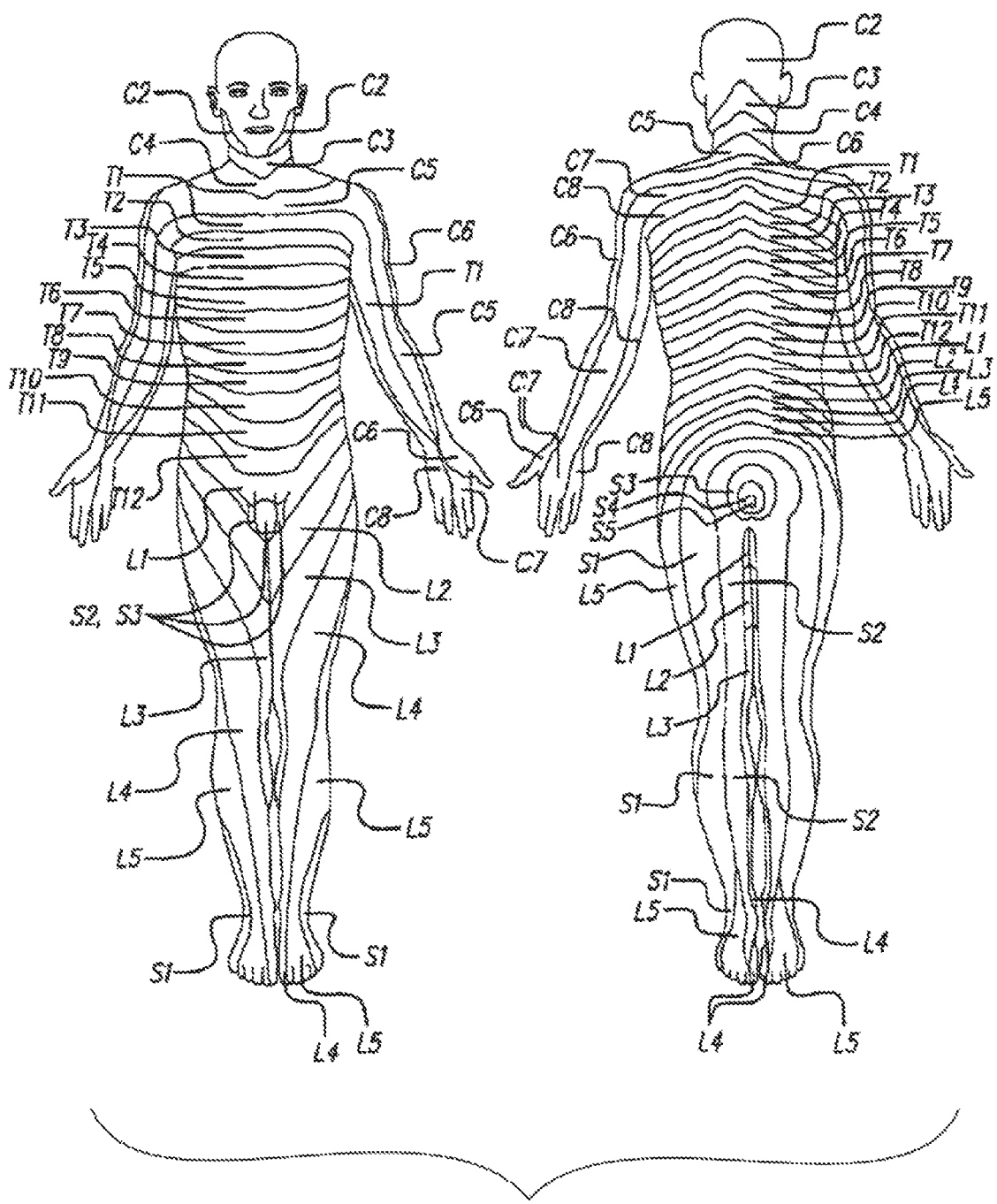
FIG. 3C illustrates the various dermatomes of the body related to their respective nerve roots in FIG. 3B.

FIG. 3B relates the spinal nerve roots to their respective vertebral spinal levels. The letter C designates nerves and vertebrae in the cervical levels. The letter T designates vertebrae and nerves in the thoracic levels. The letter L designates vertebrae and nerves in the lumbar levels. The letter S designates vertebrae and nerves in the sacral levels. FIG. 3C illustrates the various dermatomes of the body related to their respective nerve roots using the designations in FIG. 3B.

Figure 4:
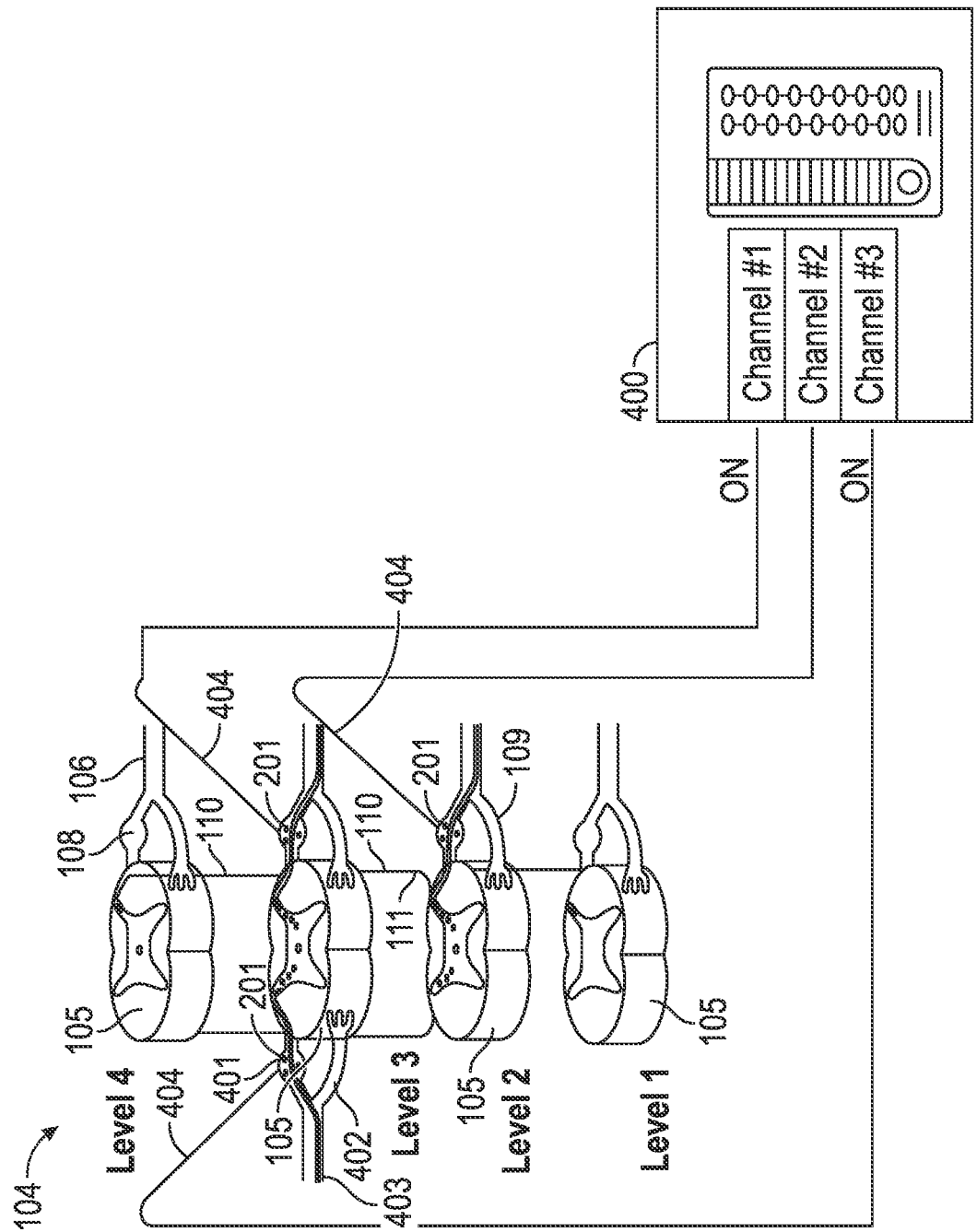
FIG. 4 illustrates a single electrode level and a two electrode level activation pattern according to an example embodiment.

FIG. 4 illustrates an example embodiment of a stimulation system that can be activated under a variety of control conditions to provide different levels and degrees of pain control. A stimulation system 400 having three electrodes 201 implanted into DRG 108 on two adjacent spinal levels. For simplicity, each spinal level illustrates a DRG 108, a ventral root 109 and a peripheral nerve 106. The exception is spinal level 3 that illustrates an additional DRG 401, a ventral root 402, and a peripheral nerve 403. The three electrodes 201 are designated channels 1, 2 and 3 by the controller 400. Each electrode is activated to provide modulation energy or signals under the control of the controller 400. Level 3 is an example of bilateral electrode placement and level 2 is an example of unilateral electrode placement. As such, the illustrated embodiment is a multi-level, unilateral and bi-lateral stimulation system. It will be understood that in other embodiments, various combinations of one or more electrodes may be placed on one or more spinal levels.

Stimulation energy is provided by a pulse generator under control of a suitable neurostimulation controller 400. Those of ordinary skill will recognize that any of a wide variety of known neurostimulation controllers may be used. Not illustrated in this view but present in the system are suitable connections between the various electrodes 201, electrode leads 404, and the controller 400. A line connecting the electrode lead 110 to the controller 400 indicates "stimulation on" communication from the controller 400 to one or more than one electrode 201.

A signal of "stimulation on" indicates any of a wide variety of stimulation patterns and degrees of stimulation. The "stimulation on" signal may be an oscillating electrical signal may be applied continuously or intermittently. Furthermore, if an electrode is implanted directly into or adjacent to more than one ganglion, the oscillating electrical signal may be applied to one electrode and not the other and vice versa. One can adjust the stimulating poles, the pulse width, the amplitude, as well as the frequency of stimulation and other controllable electrical and signally factors to achieve a desired modulation or stimulation outcome.

The application of the oscillating electrical signal stimulates the area of the nerve chain where the electrode 201 is placed. This stimulation may either increase or decrease nerve activity. The frequency of this oscillating electrical signal is then adjusted until the symptoms manifest by physiological disorder being treated has been demonstrably alleviated. This may step may be performed using patient feedback, sensors or other physiological parameter or indication. Once identified, this frequency is then considered the ideal frequency. Once the ideal frequency has been determined, the oscillating electrical signal is maintained at this ideal frequency by storing that frequency in the controller.

In one specific example, the oscillating electrical signal is operated at a voltage between about 0.5 V to about 20 V or more. More preferably, the oscillating electrical signal is operated at a voltage between about 1 V to about 30 V or even 40V. For micro stimulation, it is preferable to stimulate within the range of 1V to about 20V, the range being dependent on factors such as the surface area of the electrode. Preferably, the electric signal source is operated at a frequency range between about 10 Hz to about 800 Hz. More preferably, the electric signal source is operated at a frequency range between about 30 Hz to about 500 Hz. Preferably, the pulse width of the oscillating electrical signal is between about 25 microseconds to about 500 microseconds. More preferably, the pulse width of the oscillating electrical signal is between about 50 microseconds to about 300 microseconds.

The application of the oscillating electrical signal may be provided in a number of different ways including, but not limited to: (1) a monopolar stimulation electrode and a large area non-stimulating electrode return electrode; (2) several monopolar stimulating electrodes and a single large area non-stimulating return electrode; (3) a pair of closely spaced bi-polar electrodes; and (4) several pairs of closely spaced bi-polar electrodes. Other configurations are possible. For example, the stimulation electrode(s) of the present invention may be used in conjunction with another non-stimulating electrode—the return electrode—or a portion of the stimulation system may be adapted and/or configured to provide the functionality of a return electrode. Portions of the stimulation system that may be adapted and/or configured to provide the functionality of the return electrode include, without limitation, the battery casing or the pulse generator casing. A stimulation pattern provided to one of the electrodes positioned in level 2 or 3 produces pain blocking/relief in a region of the body.

It will be appreciated that embodiments of the present invention can stimulate specific dermatome distributions to probe which electrode or group of electrodes or combination of electrodes (including drug coated or delivery electrodes) is best positioned or correlates most closely to one or more specific areas of pain. As such, a stimulation system according to an embodiment of the present invention may be "fine-tuned" to a specific area of coverage or type of pain. The results obtained from such testing can be used to one or more stimulation or treatment regimens (i.e., series of stimulations in the presence of or in combination with a therapeutic agent from a coated electrode) for a particular patient for a particular type of pain. These pain treatment regimens may be programmed into a suitable electronic controller or computer controller system (described below) to store the treatment program, control, and monitor the system components execution of the stimulation regime as the desired therapeutic regime is executed.

It is to be appreciated that the electrode placement and blocking patterns illustrated by FIG. 4 may be modified using information such as in FIGS. 3B and 3C for targeted placement to specific portions of the body depending upon individual needs.

Micro-electrode and stimulation system embodiments of the present invention may be implanted into a single nerve root ganglion utilizing the implantation methods of the present invention. The implantation methods described herein provide numerous advantages, including but not limited to: low risk percutaneous access route similar to other procedures, direct delivery of localized quantities of pharmacological agents at the nerve root when using embodiment having electrodes coated with pharmacological agents, and electrode placement that enables preferential, selective nerve fiber stimulation.

Figure 5:
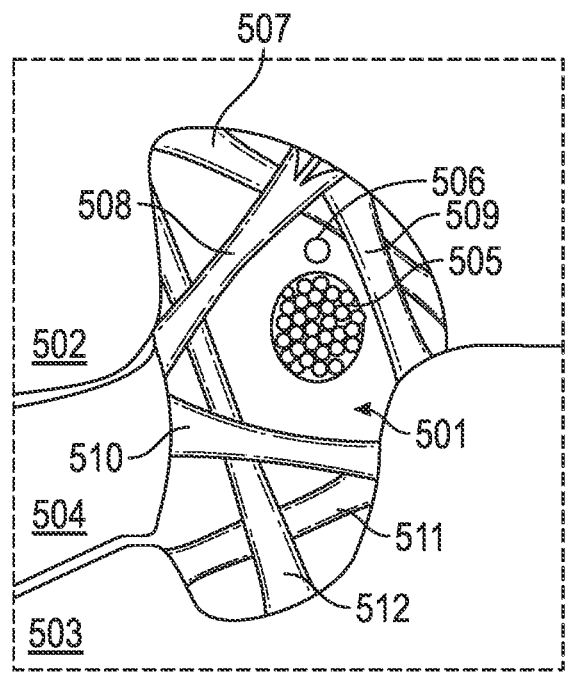
FIG. 5 is a simplified view of a neural foramen viewed from the left side.

The implantation of a stimulation lead in a position to stimulate the DRG can be a challenging percutaneous procedure. FIG. 5 is a simplified view of a neural foramen viewed from the left side. Neural foramen 501 is formed by adjacent vertebrae 502 and 503 and intervertebral disc 504. Foramen 501 is an opening at the side of the epidural space that allows passage of nerve roots and blood vessels. Nerve root 505 extends from the spinal cord (not shown) outward through foramen 501.

During the typical implant process, a surgeon may manipulate an implant tool within the epidural space to place the distal tip of the implant tool immediately adjacent to the foramen 501 associated with the DRG to be stimulated. A stimulation lead 506 is then advanced and extended out from the distal tip of the implant tool to pass through the foramen 501 along and above nerve root 505 into position adjacent to the target DRG. However, the foramen 501 is not directly visible under fluoroscopy. Instead, the surgeon estimates its position by identifying other vertebral structures that are visible via fluoroscopy. In most patients, the anatomy of foramen 501 also includes other structures, such as inferior corporopedicular ligament 507, superior transforaminal ligament 508, ligamentum flavum 509, mid-transforaminal ligament 510, inferior transforaminal ligament 511, superior corporopedicular ligament 512, and other intraforamial ligaments and vessels.

Figure 6:
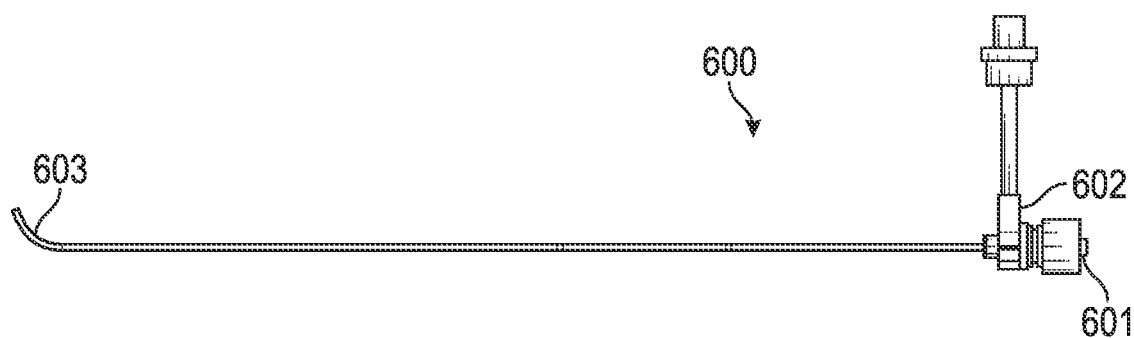
FIG. 6 depicts an implant tool for implanting a lead for DRG stimulation according to some embodiments.

In some embodiments, an implant tool is provided to assist the implant of a stimulation lead for DRG stimulation. FIG. 6 depicts implant tool 600, such as a delivery sheath, according to some embodiments. Implant tool 600 includes port 601 at its proximal end for receiving a stimulation lead to be implanted adjacent to a target DRG. Implant tool 600 includes hub 602 for grasping the tool by the implanting clinician. Also, hub 602 may include a locking mechanism such that, when hub 602 is rotated, the locking mechanism of hub 602 locks onto the stimulation lead to prevent internal movement of the lead during positioning of the tool 600. Implant tool 600 includes exit port 603 located at the distal end of implant tool 600. Implant tool 600 may be fabricated from suitable medical grade polymers according to some embodiments.

Figure 7:
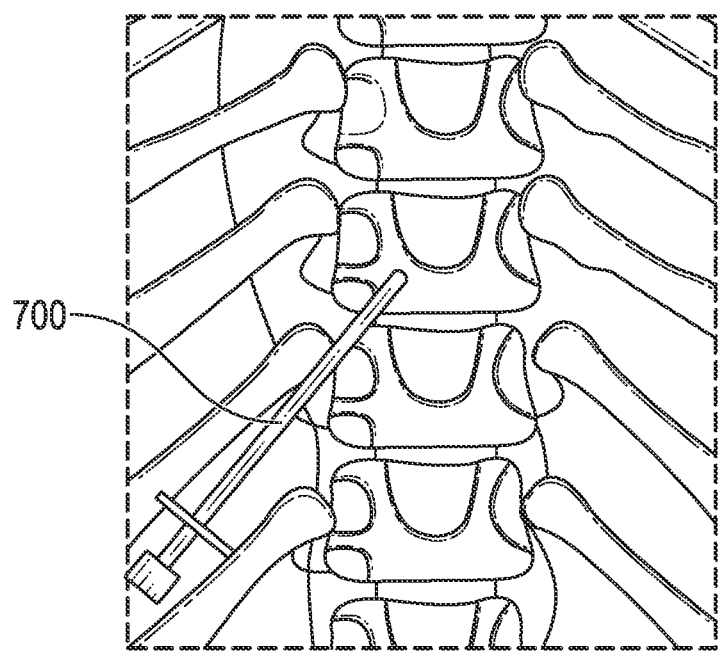
FIG. 7 depicts a needle positioned during an implant procedure according to some embodiments.

In some embodiments, the implant procedure begins by accessing the epidural space using a suitable needle 700 (e.g., a Tuohy needle) as shown in FIG. 7. The needle angle should be selected such that the eventual landing location of the distal tip of tool 600 will be the medial aspect of the pedicle above the target foramen for the DRG to be stimulated.

Figure 8:
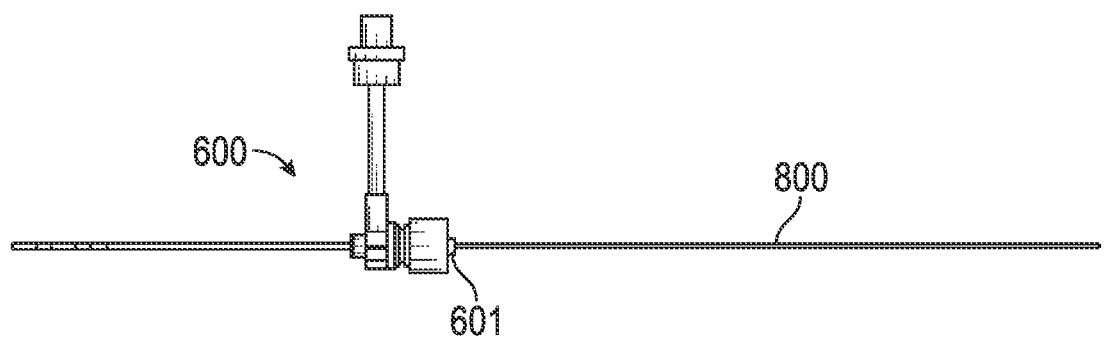
FIG. 8 depicts a DRG lead being placed in an implant tool according to some embodiments.
Figure 9:
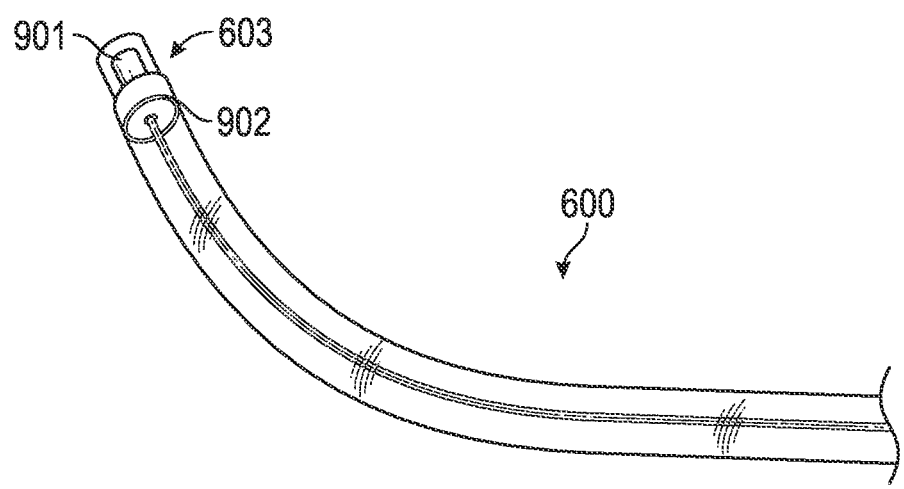
FIG. 9 depicts a distal end of the implant tool shown in FIG. 6 with a lead positioned therein for implant according to some embodiments.
Figure 10:
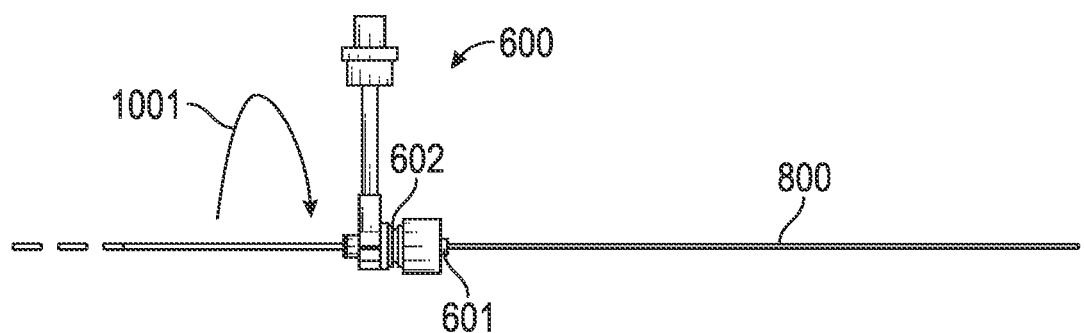
FIG. 10 depicts manipulation of the hub of the implant tool shown in FIG. 6 to lock the DRG in place according to some embodiments.

In some embodiments, stimulation lead 800 is inserted through port 601 at the proximal end of tool 600 as shown in FIG. 8. The stimulation lead 800 may include a removable stylet to assist manipulation of the distal portion of lead 800 to position electrodes of the lead into a suitable position for DRG stimulation. Also, the stylet may include a curve or bias to assist the stimulation lead to curve or bend upon deployment from tool 600. As shown in FIG. 9, which is an enlarged view of the distal end of tool 600, stimulation lead 800 is positioned within tool 600 such that the ball-tip end 901 is protruding slightly from the exit port 603. The distal end of tool 600 may also include a radiopaque marker 902 for visualization of the distal tip of tool under fluoroscopy. After the lead 800 is correctly positioned within tool 600, hub 602 is rotated (1001, FIG. 10) which engages the internal locking mechanism. The internal locking mechanism prevents lateral movement or sliding of lead 800 within tool 600 while the clinician positions tool 600 within the epidural space.

Figure 11:
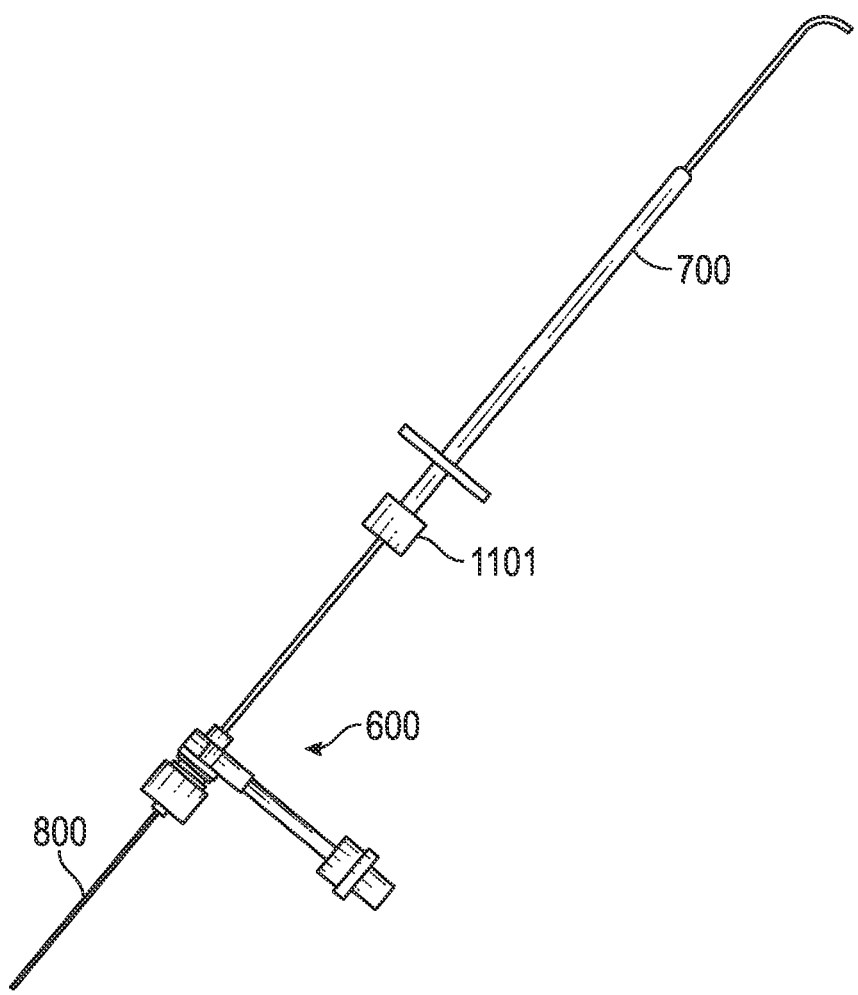
FIG. 11 depicts entry of the implant tool shown in FIG. 6 through a needle to access the epidural space according to some embodiments.
Figure 12:
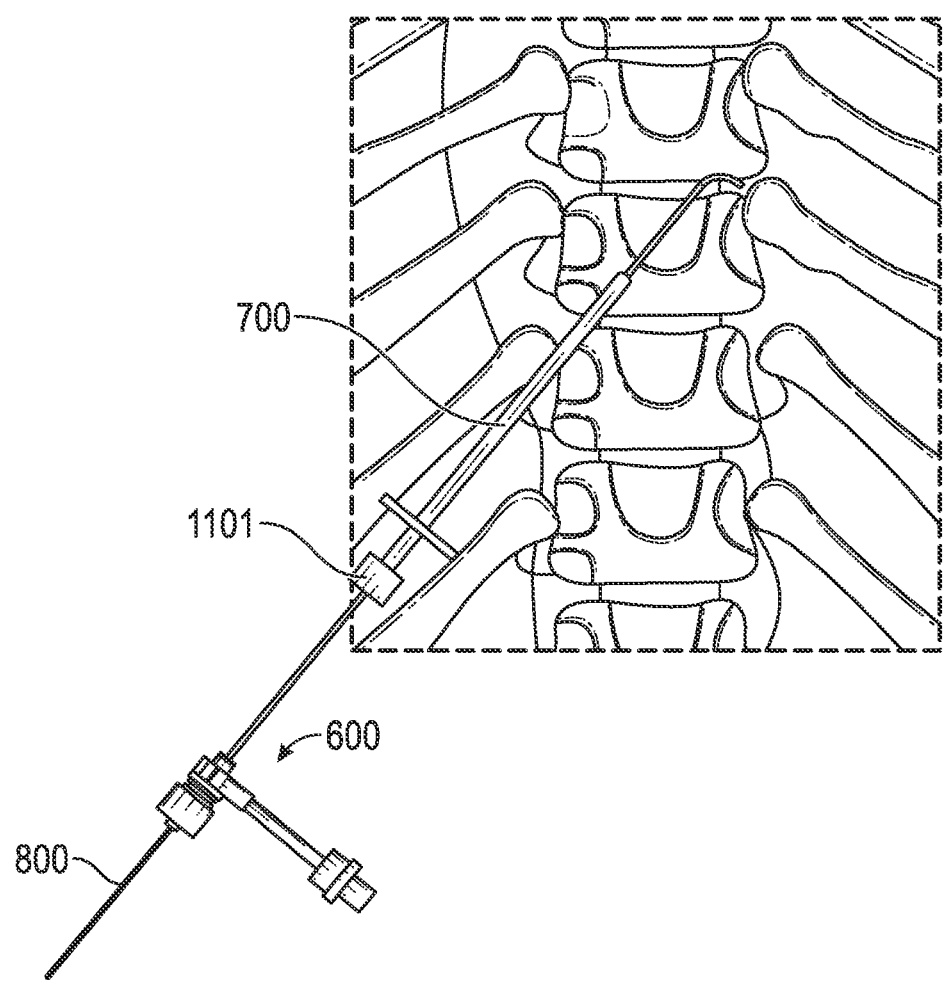
FIG. 12 depicts a path for advancement of the implant tool within the epidural space according to some embodiments.

Implant tool 600 is then inserted through the proximal end 1101 of needle 700 as shown in FIG. 11 to access the epidural space. The clinician advances tool 600 within the epidural space of the patient as shown in FIG. 12. The clinician may observe the advancement of marker 902 using fluoroscopy. The clinician continues advancement of tool 600 until the distal tip of tool 600 comes into contact with the medial aspect of the pedicle. When the distal tip of tool 600 contacts this defined structural landmark, the clinician receives tactile confirmation that the tool 600 is positioned correctly for deployment of lead 800.

Figure 13:
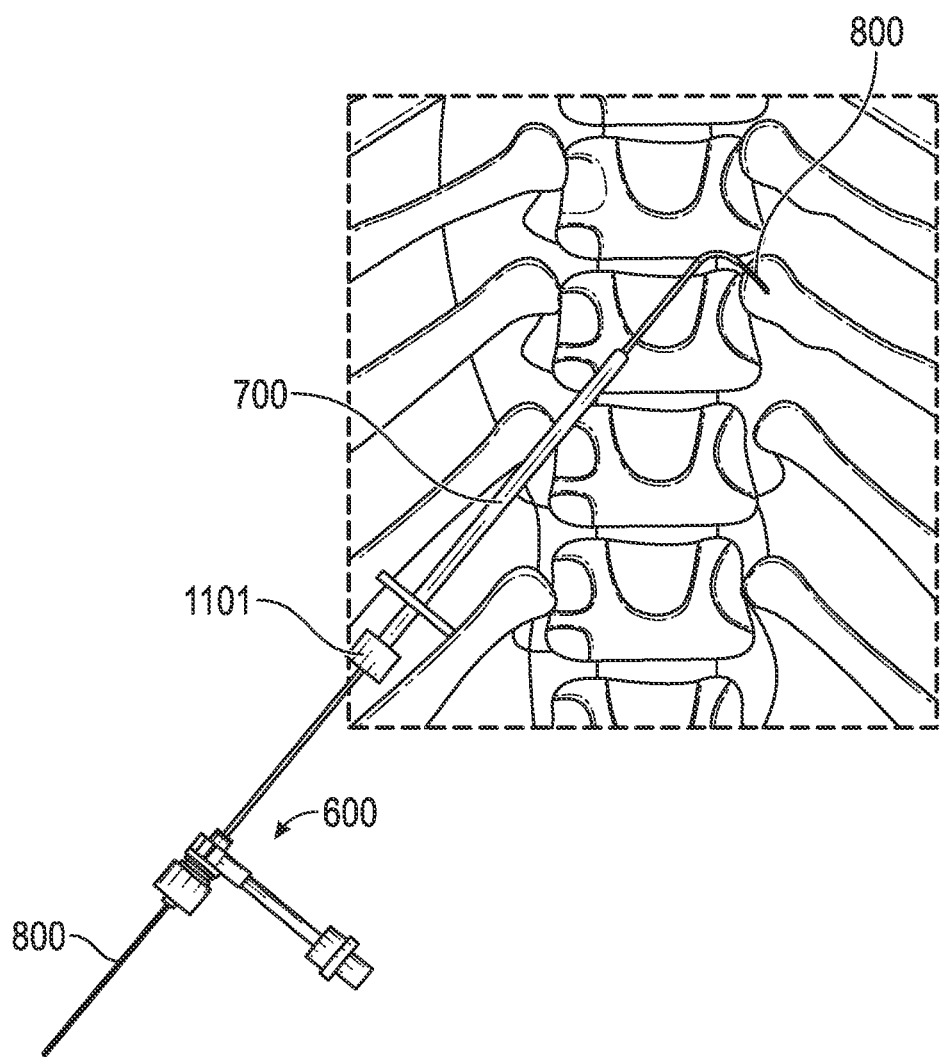
FIG. 13 depicts advancement of a DRG lead from the implant tool through a foramen according to some embodiments.

When the distal tip of tool 600 is properly positioned, hub 602 is rotated back to the unlocked position. Lead 800 is advanced through the tool 600 causing the distal tip of lead 800 to exit port 603. An interior surface of tool 600 near port 603 may be angled or curved to direct the distal tip of lead 800 as it is advanced out of port 603. Due to the position of the distal tip 600 and the use of port 603, lead 800 is positioned to proceed through the foramen as shown in FIG. 13 for positioning adjacent to the target DRG. The advancement of the lead 800 continues until the electrodes of the leads are suitably positioned to stimulate the DRG.

Electrode placement within the DRG may be confirmed using neurodiagnostic testing techniques such as somatosensory evoked potential (SSEP) and electromyography (EMG) adapted for the methods and systems described herein. One illustrative example includes the placement of sensing electrodes in the sensory nervous system above and below the DRG level having the implanted electrode(s). Test stimulation is applied to the DRG using one or more electrodes of the lead and the voltage potential at the sensory (SSEP or EMG) electrodes is measured above and below the targeted DRG to confirm that the electrodes of lead 800 are implanted adjacent to the targeted DRG. The test stimulation may range from 0.4 v to 0.8v at 50 Hz to evoke the physiological response for measurement by the sensory electrodes.

Figure 14:
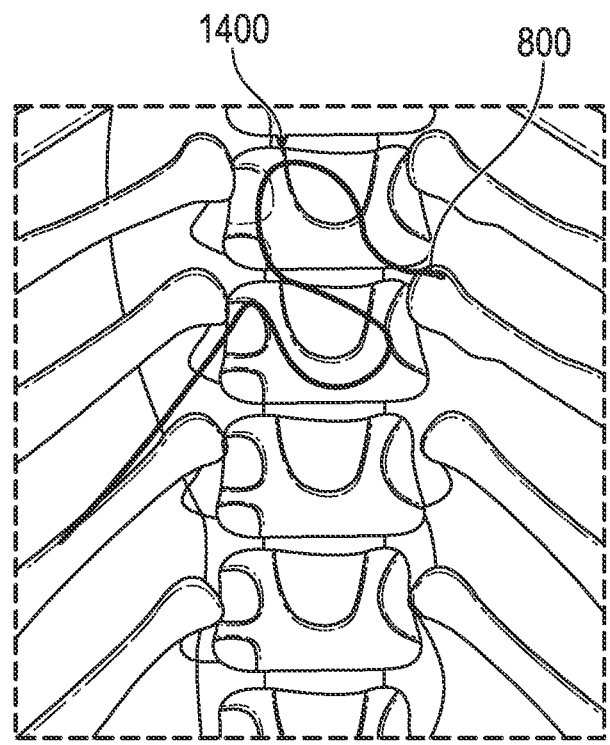
FIG. 14 depicts creation of an "S-loop" shape for the lead body of an implanted DRG lead to stabilize the DRG lead according to some embodiments.

Using current techniques, once the electrodes are properly positioned, one or more undulations or an "S-curve" configuration 1400 as shown in FIG. 14 may be created in the lead 800 within the epidural space to stabilize the lead's position and to reduce migration. The undulations are used to help keep the electrodes on lead 800 at the target DRG site to properly stimulate the DRG to get the desired therapy. The creation of the undulations 1400 may occur by a combination of pulling and twisting tool 600 while pushing and/or pulling the lead 800 and/or stylet. Additional details regarding creation of lead stabilizing shape are discussed in U.S. Patent Publication No. 2011/0276056, which is incorporated herein by reference. In prior systems, the S-curve is necessary is to provide strain relief and to prevent migration of the lead 800 into the epidural space due to a lack of anchor within the epidural space. Prior systems do not provide for an anchor at the distal end of the lead 800 in the region near the DRG.

Additionally, the lead 800 is anchored using, for example, is a slide-on cylindrical anchor made from a medical grade silicone. This anchor may be placed around the terminal end of the lead 800 and slid down the lead into the needle puncture site, which is located just subcutaneous. The anchor is then tied down to either the fascia or interspinous ligament using sutures. When the sutures are tied around the silicone anchor, the silicone material deflects inward and grabs onto the lead 800.

Anchoring of percutaneous DRG leads is difficult due to anatomical and tooling challenges. If the lead moves, the change in electrode location will affect the ability to provide the desired therapy. Existing silicon anchors are placed outside of the epidural space at a location approximately 5-8" away from the therapy location. As a result, there are several tissue transitions between the anchor and the therapy region, including the epidural space and the foraminal ligaments.

The embodiments described herein use an anchor that can be placed significantly closer to the therapy location, thereby ensuring that the electrical contacts do not move from the therapeutic zone of the DRG. This anchor is placed in the foramen and attaches to the naturally occurring foraminal ligaments. The foraminal ligament anchor may be deployed using the same or similar tools as are currently used to deploy the stimulation lead 800. Additionally, use of the foraminal ligament anchor may reduce the need for the S-curve configuration 1400, subcutaneous anchoring, and other time-consuming tasks that are currently part of the clinical workflow.

Figure 15:
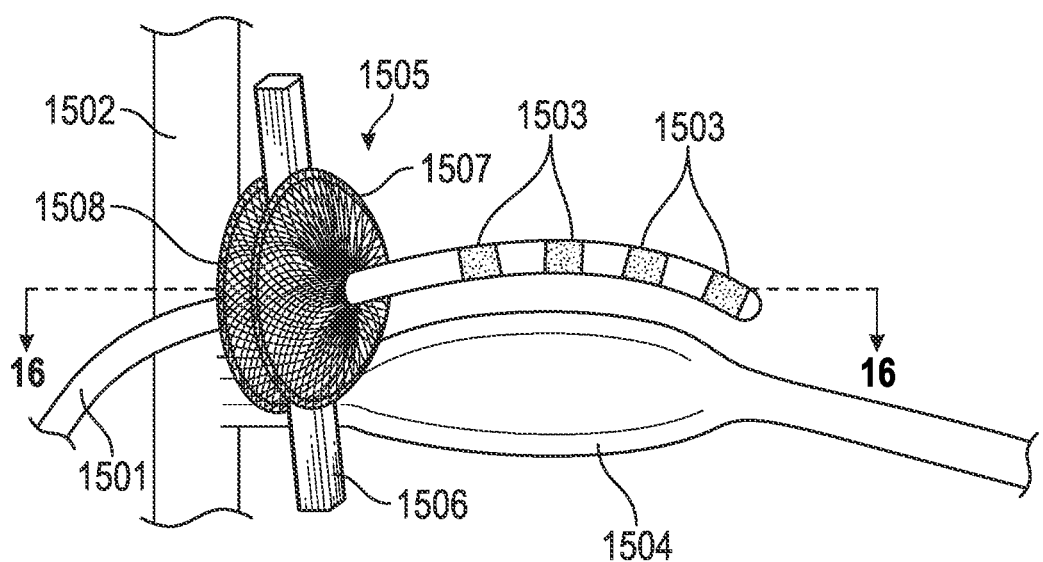
FIG. 15 illustrates a foraminal ligament anchor deployed in a configuration to hold an electrode lead in position near a DRG according to an example embodiment.

FIG. 15 illustrates a foraminal ligament anchor deployed in a configuration to hold a stimulation lead in position near a DRG according to an example embodiment. A stimulation lead 1501 is deployed though the epidural space along spinal cord 1502 and into the foramen using the percutaneous procedure described above. Lead 1501 is positioned so that electrodes 1503 are near a target DRG 1504. The lead 1501 is generally configured to transmit one or more electrical signals from an implantable pulse generator (IPG) (not shown) for application at, or proximate to, DRG 1504 via electrodes 1503. Stimulation lead 1501 is held in position using anchor 1505, which is attached to a foraminal ligament 1506. Anchor 1505 comprises two expandable disks—distal disk 1507 and proximal disk 1508—that expand on opposite sides of foraminal ligament 1505 and that grip onto lead 1501 when deployed. The disks 1507, 1508 are in a collapsed configuration while being deployed and then are expanded once in a desired position.

Figure 16:
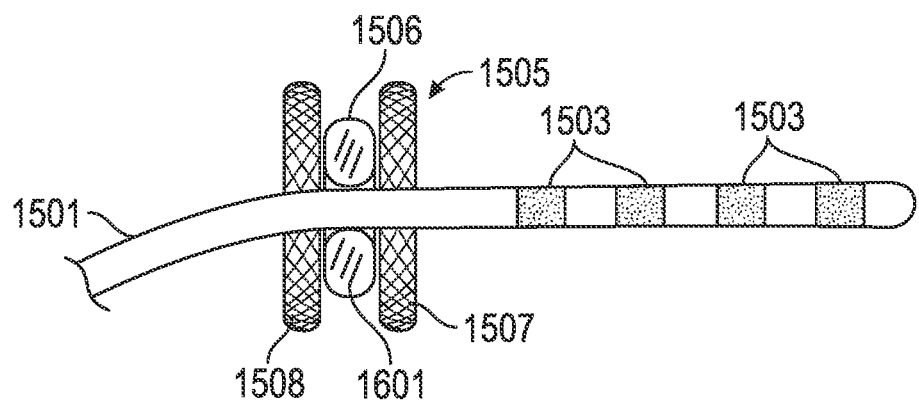
FIG. 16 is a cross section view of FIG. 15 showing the anchor attached to a foraminal ligament to hold an electrode lead.

FIG. 16 is a cross section view of FIG. 15 showing the anchor attached to a foraminal ligament to hold a stimulation lead. Ligament 1506 may be any foraminal ligament or web of ligaments that are advantageously positioned to act as an anchoring structure while deploying the lead 1501. An implant tool may be used to pierce the web of foraminal ligaments 1506 to create an opening 1601, which allows stimulation lead 1501 to pass through ligaments 1506. Once stimulation lead 1501 is positioned so that electrodes 1503 are near the target DRG 1504, anchor 1505 may be deployed with disks 1507 and 1508 on either side of ligaments 1506. In one embodiment, distal disk 1507 is expanded first and proximal disk 1508 is expanded second. Once expanded, distal disk 1507 prevents stimulation lead 1501 from moving proximally back through opening 1601, and proximal disk 1508 prevents lead 1501 from moving further forward through opening 1601. During expansion, disks 1507 and 1508 grip onto stimulation lead 1501 so that disks 1507 and 1508 are fixed to set positions on lead 1501, which anchors stimulation lead 1501 in a set position relative to ligaments 1506 and thereby hold electrodes 1503 in position relative to DRG 1504.

Figure 17:
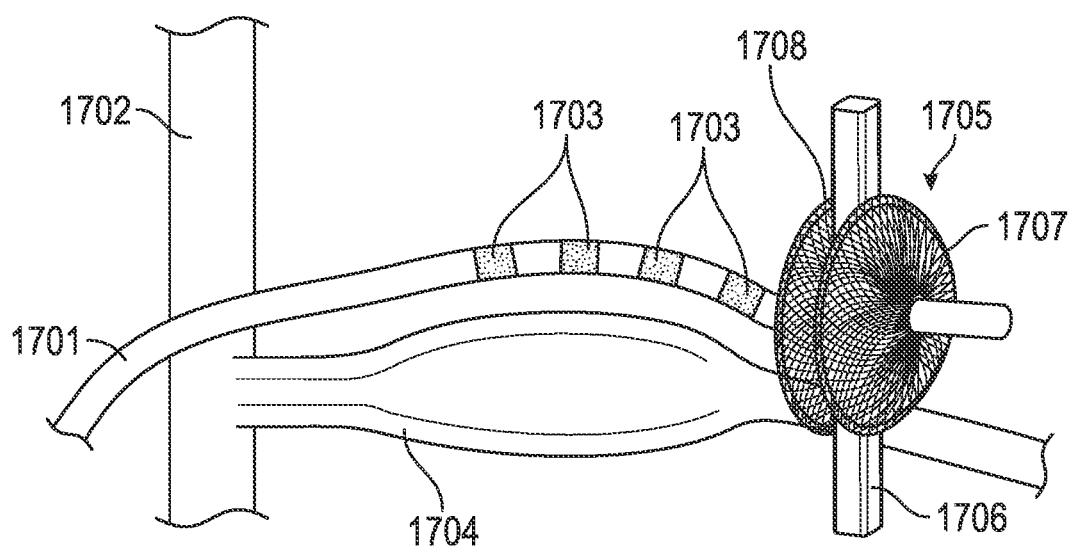
FIG. 17 illustrates a foraminal ligament anchor deployed in an alternative configuration to hold a stimulation lead in position near a DRG according to another example embodiment.

FIG. 17 illustrates a foraminal ligament anchor deployed in an alternative configuration to hold a stimulation lead in position near a DRG according to another example embodiment. A stimulation lead 1701 is deployed though the epidural space along spinal cord 1702 and into the foramen. Lead 1701 is positioned so that electrodes 1703 are near a target DRG 1704. Stimulation lead 1701 is held in position using anchor 1705, which is attached to a foraminal ligament 1706. Due to the location of ligament 1706 in the patient's anatomy, anchor 1705 is positioned distal to electrodes 1703 and DRG 1704. Distal disk 1707 and proximal disk 1708 of anchor 1705 clamp onto opposite sides of foraminal ligament 1705 and grip onto lead 1701 when deployed.

It will be understood that in other embodiments, the foraminal ligament anchor may be placed anywhere along the stimulation lead as appropriate for secure attachment to an available foraminal ligament based upon the patient's anatomy. For example, in other embodiments, the foraminal ligament anchor may be positioned over or between the stimulation lead electrodes (e.g., 1503, 1703) when the patient's anatomy requires such positioning.

According to one embodiment, the foraminal ligament anchor (e.g., 1505, 1705) comprises two disks each having at least one layer of metal fabric formed by a plurality of wire strands having a predetermined relative orientation with respect to one another. The strands may be braided, interwoven, or otherwise combined to define a generally tubular fabric. However, it is understood that according to additional embodiments, the foraminal ligament anchor may be formed using various techniques. For example, the disks could be etched or laser cut from a tube such as to form an interstice geometry.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. A factor in choosing a suitable material for the wires strands is that the wires retain a suitable amount of the deformation induced by the molding surface (as described below) when subjected to a predetermined heat treatment and elastically return to said molded shape after substantial deformation.

Materials that may be suitable for this purpose may include a cobalt-based low thermal expansion alloy referred to in the field as Elgiloy, nickel-based high temperature high-strength "superalloys" commercially available from Haynes International under the trade name Hastelloy, nickel-based heat treatable alloys sold under the name Incoloy by International Nickel, and a number of different grades of stainless steel. One class of materials that meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter.

In forming a medical device according to one embodiment of the present invention, an appropriately sized piece of the fabric is cut from the larger piece of fabric, which is formed, for example, by braiding wire strands to form a long tubular braid. When cutting the fabric to the desired dimensions, care should be taken to ensure that the fabric will not unravel. One can use a number of methods, including solder, braze, weld, coat, glue, clamp, tie or otherwise affix the ends of the desired length together (e.g., with a biocompatible cementitious organic material).

Figure 18A:
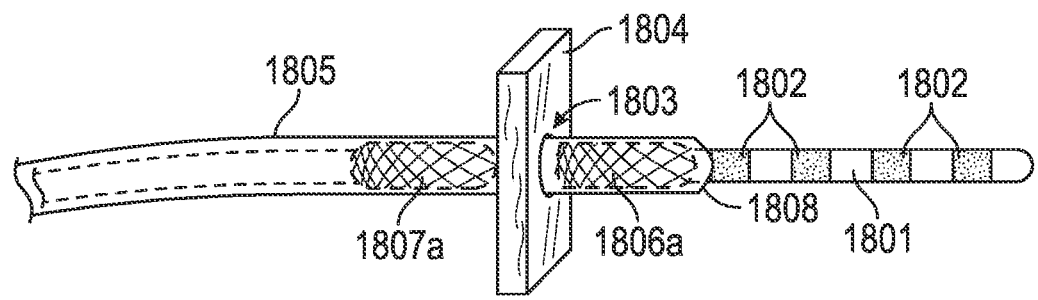
FIGS. 18A-C illustrate deployment of a foraminal ligament anchor according to one example embodiment.
Figure 18B:
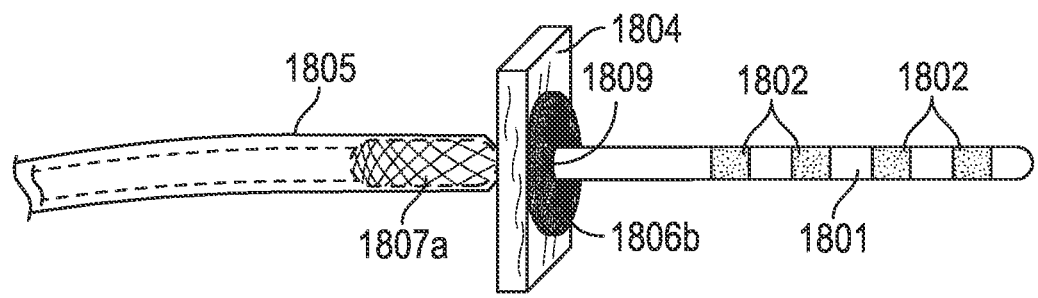
Figure 18C:
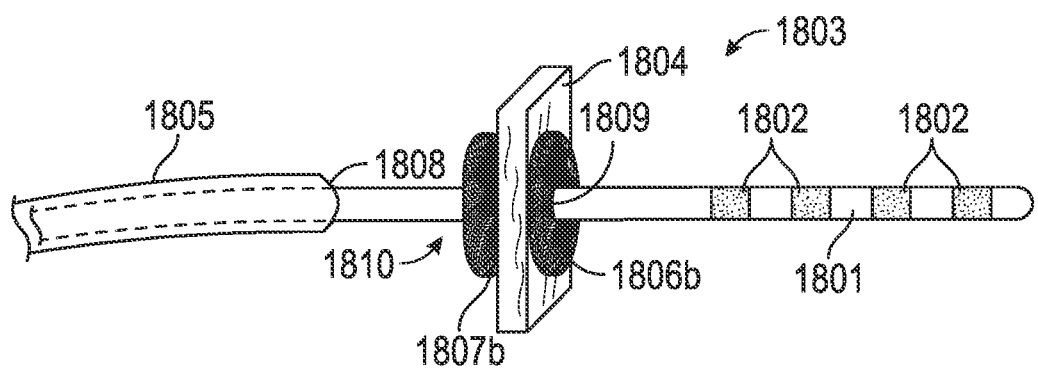

FIGS. 18A-C illustrate deployment of a foraminal ligament anchor according to one example embodiment. In FIG. 18A, stimulation lead 1801 has been previously deployed so that electrodes 1802 are positioned near a target DRG. Stimulation lead 1801 has been routed through an opening 1803 in foraminal ligaments 1804. The opening 1803 may have been formed, for example, by popping through a web of ligaments 1804 using an implant tool during deployment of stimulation lead 1801. An anchor deployment tool 1805 may be routed through the opening 1803 using stimulation lead 1801 as a guide wire. A foraminal ligament anchor, which comprises a distal disk 1806 and a proximal disk 1807, is carried by anchor deployment tool 1805, which may be a catheter, for example. The disks 1806a and 1807a surround stimulation lead 1801 and are in a collapsed configuration while within deployment tool 1805. The deployment tool 1805 advances along stimulation lead 1801 until distal disk 1806a has been moved through hole 1803 to the distal side of ligament 1804. Alternatively, deployment tool 1805 may be positioned and then disks 1806a and 1807a may be advanced along stimulation lead 1801 within deployment tool 1805.

In FIG. 18B, anchor deployment tool 1805 is retracted and distal disk 1806 remains on the distal side of ligament 1804. Alternatively, deployment tool 1805 may be positioned with its opening 1808 just on the distal side of ligament 1804, and distal disk 1806a may be advanced along stimulation lead 1801 and out of deployment tool 1805. As distal disk 1806a is exposed from inside tool 1805, it expands into a disk-shape 1806b. When expanded, distal disk 1806b is too large to move back through hole 1803. As it expands, the central opening 1809 in distal disk 1806b grips on stimulation lead 1801, which fixes the position of distal disk 1806b relative to stimulation lead 1801.

In FIG. 18C, anchor deployment tool 1805 is further retracted and expanded distal disk 1806b remains on the distal side of ligament 1804. As deployment tool 1805 is moved away from ligament 1804, proximal disk 1807a remains along the proximal side of ligament 1804. Alternatively, deployment tool 1805 may be positioned with its opening 1808 spaced away from the proximal side of ligament 1804, and proximal disk 1807a may be advanced along stimulation lead 1801 and out of deployment tool 1805. As distal disk 1807a is exposed from inside tool 1805, it expands into a disk-shape 1807b. When expanded, distal disk 1807b is too large to move forward through hole 1803. As it expands, the central opening 1810 in proximal disk 1807b grips on stimulation lead 1801, which fixes the position of proximal disk 1807b relative to stimulation lead 1801.

Together, the expanded distal disk 1806b and expanded proximal disk 1807b from the foraminal ligament anchor. By fixing the position of distal disk 1806b and proximal disk 1807b relative to stimulation lead 1801, the stimulation lead 1801 is also fixed in position relative to ligament 1804. Distal disk 1806b prevents proximal movement of stimulation lead 1801 relative to ligament 1804, and proximal disk 1807b prevent distal movement of stimulation lead 1801 relative to ligament 1804, which has the effect of anchoring stimulation lead 1801 to ligament 1804. In turn, this anchors electrodes 1802 in their initial deployed position relative to a target DRG and limits further movement of electrodes 1802 over time, thereby increasing likelihood that electrodes 1802 will remain in a desired therapeutic location.

In another embodiment, only the distal disk 1806b is deployed, which prevents stimulation lead 1801 from moving back through ligament 1804. Instead of using a proximal disk 1807 to prevent further forward movement of stimulation lead 1801, the stimulation lead may be anchored to other anatomy on the proximal side of ligament 1804, such as suturing or otherwise tying down the stimulation lead 1801 to the fascia or an interspinous ligament.

Figure 19A:
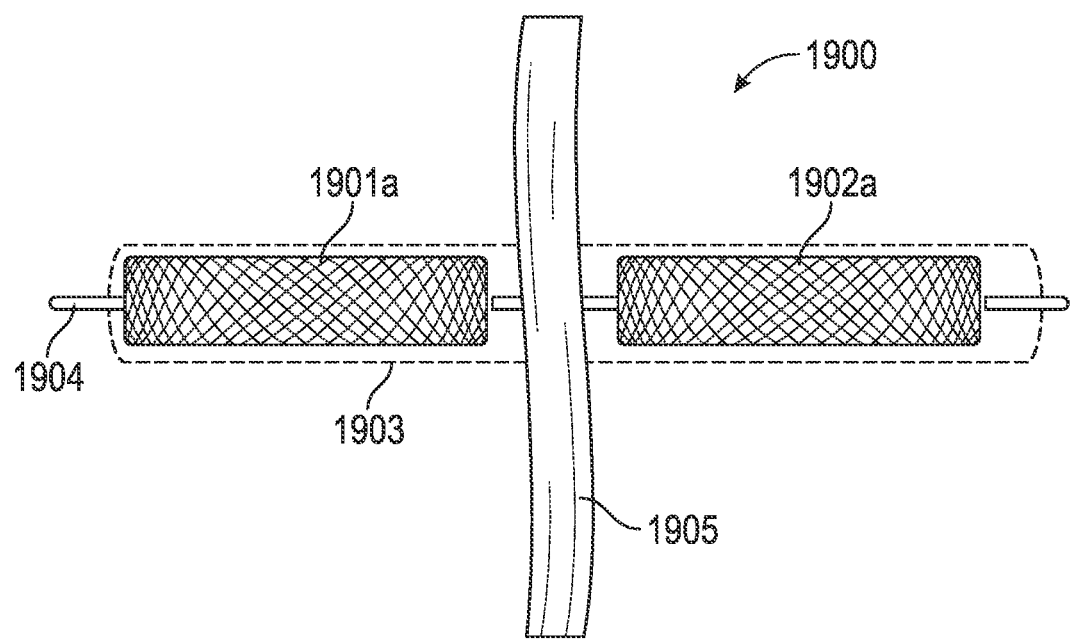
FIGS. 19A-B illustrate deployment of a foraminal ligament anchor having two independent disk segments.
Figure 19B:
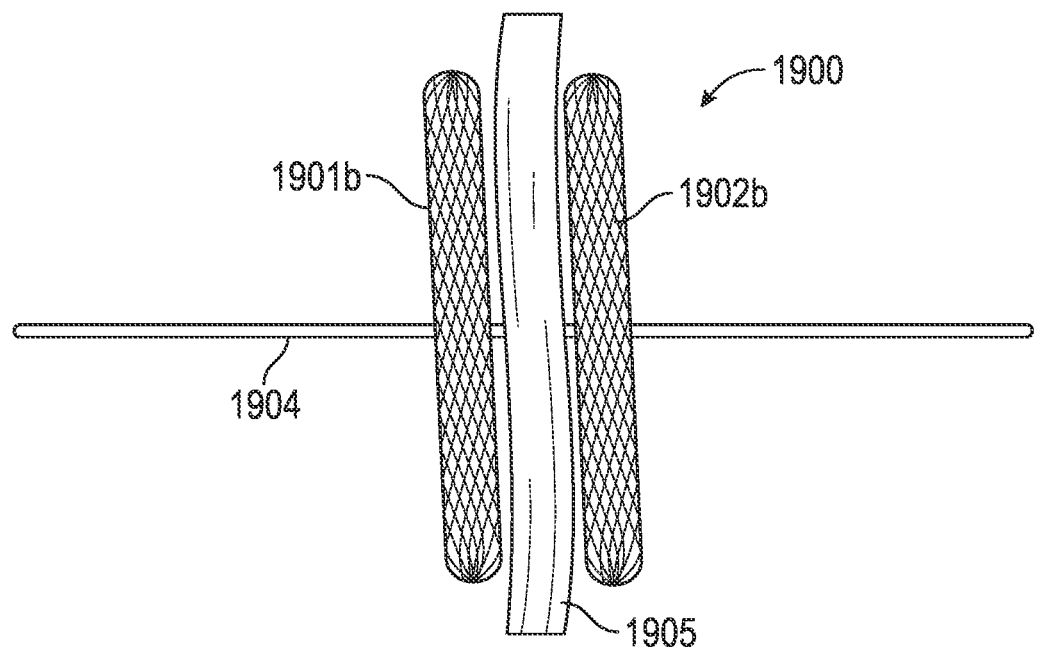

In some embodiments, each segment of the anchor may be advanced individually through the delivery catheter and separately deployed on opposite sides of a foraminal ligament. For example, referring to FIGS. 19A and 19B, a foraminal ligament anchor 1900 comprises two segments that are initially compressed 1901a, 1902a while they are advanced within a deployment catheter tool 1903. Segments 1901a, 1902a may be advanced together or separately along guidewire 1904, which may be a stimulation lead in one embodiment. Segment 1901a is advanced through a hole in foramen ligaments 1905 and then deployment catheter 1903 is withdrawn. The segments become unconstrained on exiting the distal end of the catheter, whereupon each segment resiliently returns to its predefined, relaxed, disk-like shape 1901b, 1902b. The segments 1901b and 1902b may be deployed individually so that they are close against opposite sides of ligaments 1905.

Figure 20A:
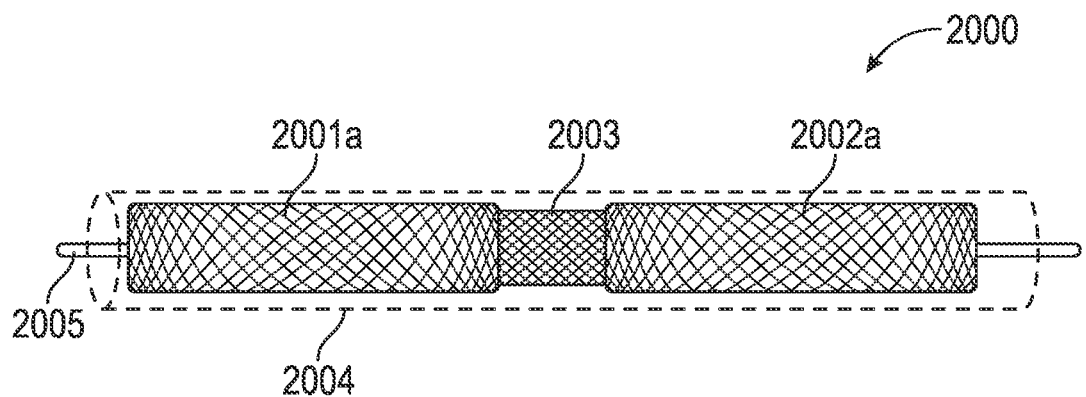
FIGS. 20A-B illustrate deployment of a foraminal ligament anchor having two disk segments that are joined by a center connector.
Figure 20B:
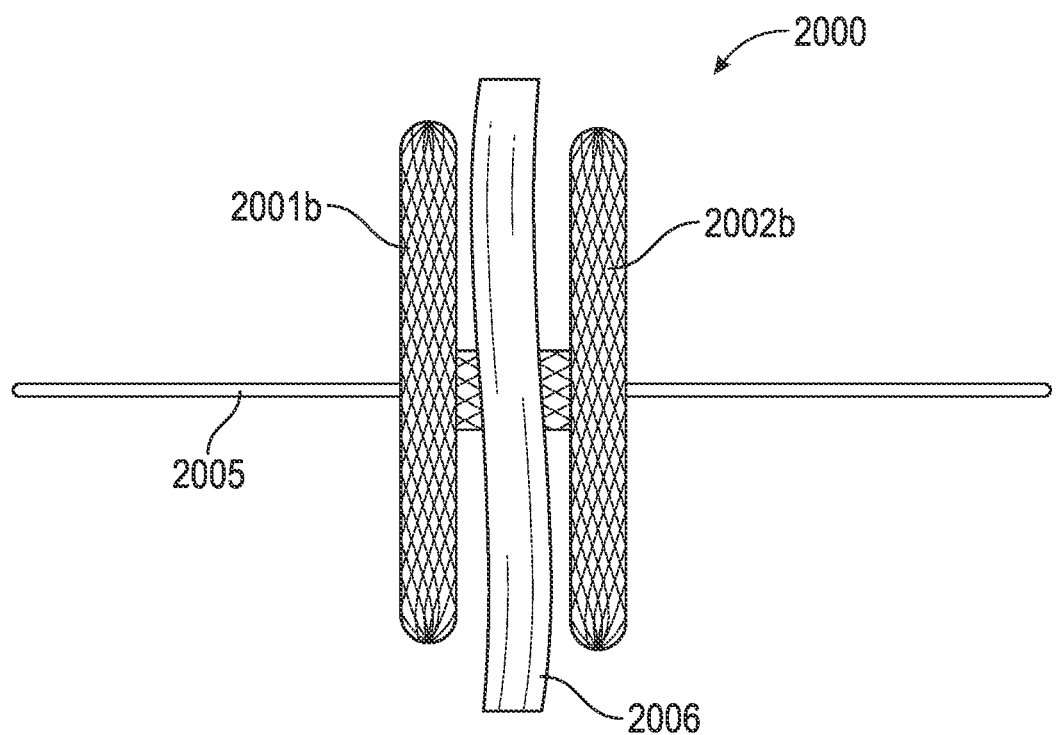

In other embodiments, the anchor may be a single component with the segments joined by a central connector. For example, referring to FIGS. 20A and 20B, a foraminal ligament anchor 2000 comprises two segments 2001, 2002 that are coupled by a connector 2003. Segments 2001a, 2002a are initially compressed while the anchor 2000 is advanced within deployment catheter 2004 along guidewire 2005, which may be a stimulation lead in one embodiment. Segment 2001a is advanced through a hole in a web of foramen ligament 2006. When the deployment catheter 2004 is withdrawn, segments 2001b and 2002b become unconstrained on exiting the distal end of the catheter 2004. Each segment 2001b and 2002b returns to its predefined, disk-like shape. Center connector 2003 holds the segments 2001b and 2002b in a consistent spaced relationship. When deployed, the segments 2001b and 2002b are on opposite sides of foramen ligaments 2006. The length of center connector 2003 may determine how close each segment 2001b and 2002b is held against foramen ligament 2006.

Once the stimulation lead is implanted with its electrodes in position to stimulate the target DRG, the lead is connected to an IPG either directly or indirectly using an extension connector. The IPG is programmed to generate electrical pulses according to a suitable neurostimulation program and the pulses are applied to the DRG using one or more electrodes of the implanted lead.

Figure 21:
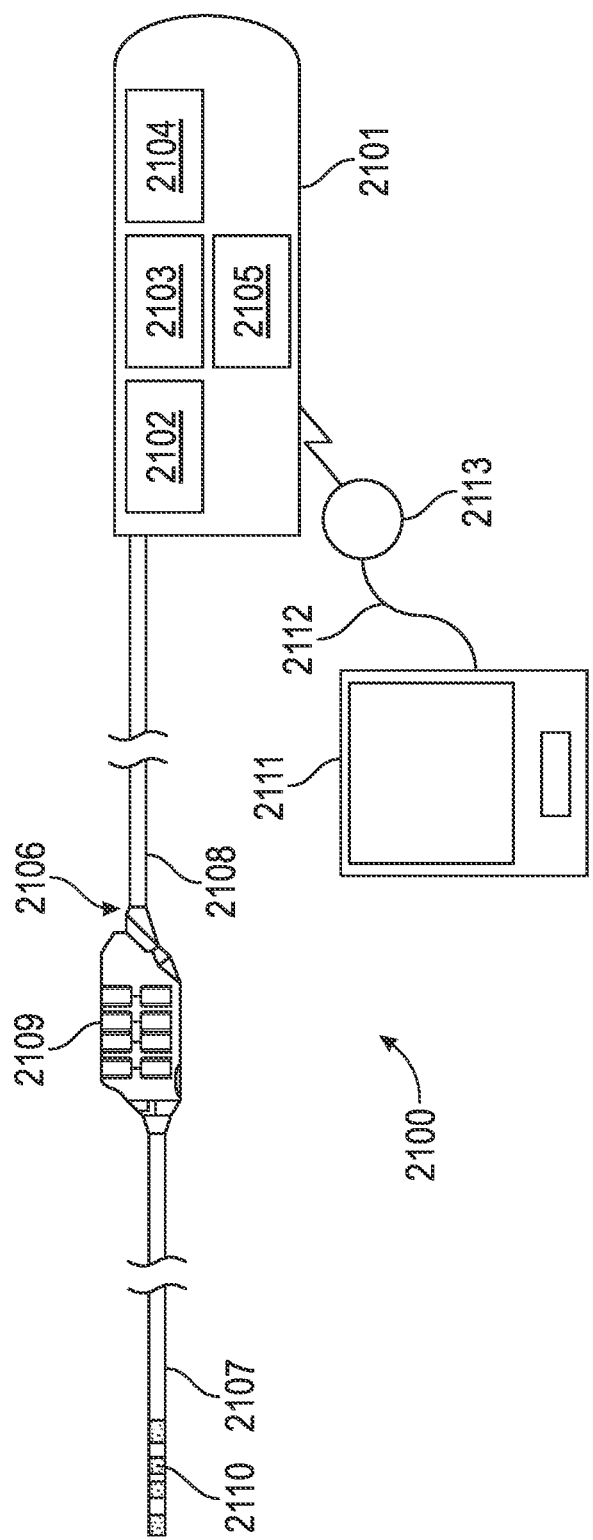
FIG. 21 depicts a system for stimulation one or more DRGs according to some embodiments.

FIG. 21 depicts a neurostimulation system that may be employed according to some embodiments. Stimulation system 2100 generates electrical pulses for application to tissue of a patient, or subject, according to one embodiment. Stimulation system 2100 includes an IPG 2101 that is adapted to generate electrical pulses for application to tissue of a patient. Implantable pulse generator 2101 typically includes a metallic housing that encloses a controller 2102, pulse generating circuitry 2103, a battery 2104, and far-field and/or near field communication circuitry 2105, and other appropriate circuitry and components of the device. Controller 2102 typically includes a microcontroller or other suitable processor for controlling the various other components of the device. Software code is typically stored in memory on implantable pulse generator 2101 for execution by the microcontroller or processor to control the various components of the device (e.g., code to implement operations discussed herein). The software code stored in memory of pulse generator 2101 may support operations of embodiments disclosed herein. Communication circuitry 2105 may include far field and/or near field communication circuitry. In some embodiments, circuitry 2105 includes low energy BLUETOOTH® communication circuitry.

Implantable pulse generator 2101 may comprise one or more attached extension components 2106 or be connected to one or more separate extension components 2106. Alternatively, one or more stimulation leads 2107 may be connected directly to implantable pulse generator 2101. Within implantable pulse generator 2101, electrical pulses are generated by pulse generating circuitry 2103 and are provided to switching circuitry. The switching circuit connects to output wires, traces, lines, or the like (not shown) which are, in turn, electrically coupled to internal conductive wires (not shown) of a lead body 2108 of extension component 2106. The conductive wires, in turn, are electrically coupled to electrical connectors (e.g., "Bal-Seal" connectors) within connector portion 2109 of extension component 2106. The terminals of one or more stimulation leads 2107 are inserted within connector portion 2109 for electrical connection with respective connectors. Thereby, the pulses originating from implantable pulse generator 2101 and conducted through the conductors of lead body 2108 are provided to stimulation lead 2107. The pulses are then conducted through the conductors of stimulation lead 2107 and applied to tissue of a patient via electrodes 2110. Any suitable known or later developed design may be employed for connector portion 2109.

For implementation of the components within implantable pulse generator 2101, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 2101. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 2107 may include a lead body of insulative material about a plurality of conductors within the material that extend from a proximal end of stimulation lead 2107 to its distal end. The conductors electrically couple a plurality of electrodes 2110 to a plurality of terminals (not shown) of stimulation lead 2107. The terminals are adapted to receive electrical pulses and the electrodes 2110 are adapted to apply stimulation pulses to tissue of the patient. Also, sensing of physiological signals may occur through electrodes 2110, the conductors, and the terminals. Additionally, or alternatively, various sensors (not shown) may be located near the distal end of stimulation lead 2107 and electrically coupled to terminals through conductors within the lead body 2108. Stimulation lead 2107 may include any suitable number of electrodes 2110, terminals, and internal conductors. Commercially available stimulation leads include the SlimTip™ DRG lead (Abbott, Plano TX).

Controller device 2111 (shown in FIG. 21) may be implemented to recharge battery 2104 of implantable pulse generator 2101 (although a separate recharging device could alternatively be employed). A "wand" 2112 may be electrically connected to controller device 2111 through suitable electrical connectors (not shown). The electrical connectors are electrically connected to a "primary" coil 2113 at the distal end of wand 2112 through respective wires (not shown). Typically, primary coil 2113 is connected to the wires through capacitors (not shown). Also, in some embodiments, wand 2112 may comprise one or more temperature sensors for use during charging operations.

The patient then places the primary coil 2113 against the patient's body immediately above the secondary coil (not shown), i.e., the coil of the implantable medical device. Preferably, the primary coil 2113 and the secondary coil are aligned in a coaxial manner by the patient for efficiency of the coupling between the primary and secondary coils. Controller device 2111 generates an AC-signal to drive current through primary coil 2113 of wand 2112. Assuming that primary coil 2113 and secondary coil are suitably positioned relative to each other, the secondary coil is disposed within the field generated by the current driven through primary coil 2113. Current is then induced in secondary coil. The current induced in the coil of the implantable pulse generator is rectified and regulated to recharge battery of implantable pulse generator 2101. The charging circuitry may also communicate status messages to controller device 2111 during charging operations using pulse-loading or any other suitable technique. For example, controller device 2111 may communicate the coupling status, charging status, charge completion status, etc.

External controller device 2111 is also a device that permits the operations of implantable pulse generator 2101 to be controlled by user after implantable pulse generator 2101 is implanted within a patient, although in alternative embodiments separate devices are employed for charging and programming. Also, multiple controller devices may be provided for different types of users (e.g., the patient or a clinician). Controller device 2111 can be implemented by utilizing a suitable handheld processor-based system that possesses wireless communication capabilities. Software is typically stored in memory of controller device 2111 to control the various operations of controller device 2111 (e.g., code to implement operations discussed herein). The software code stored in memory of device 2111 may support the operations according to embodiments disclosed herein. Also, the wireless communication functionality of controller device 2111 can be integrated within the handheld device package or provided as a separate attachable device. The user interface functionality of controller device 2111 is implemented using suitable software code for interacting with the user and using the wireless communication capabilities to conduct communications with implantable pulse generator 2101.

Controller device 2111 preferably provides one or more user interfaces to allow the user to operate implantable pulse generator 2101 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 2101 modifies its internal parameters in response to the control signals from controller device 2111 to vary the stimulation characteristics of stimulation pulses transmitted through stimulation lead 2107 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Pulse generator device 2101 and controller device 2111 may be adapted to apply different types of neurostimulation. One or more stimulation sets or programs may be defined with tonic stimulation. Also, these devices may support burst stimulation as disclosed in U.S. Pat. No. 8,934,981, entitled "SPINAL CORD STIMULATION TO TREAT PAIN," which is incorporated herein by reference. In burst stimulation, groups of pulses are provided at a relatively high frequency (greater than 250 Hz) with adjacent groups of pulses separated by a quiet period. The groups are repeated at a relatively lower frequency (e.g., 40 Hz or other physiologically relevant frequencies). These devices may support "noise" stimulation such as described in U.S. Pat. No. 9,498,634, entitled "USE OF A NEW STIMULATION DESIGN TO TREAT NEUROLOGICAL DISORDER," which is incorporated herein by reference. These devices may also support high frequency stimulation (e.g., 1500 Hz-20,000 Hz).

Example commercially available neurostimulation systems include the PROTEGE™, PRODIGY™, PROCLAIM™, INFINITY™, AXIUM™ pulse generators and CLINICIAN PROGRAMMER APP from Abbott Laboratories.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 45 U.S.C. § 112(f), unless and until such claim limitations expressly use the phrase "means for" followed by a statement of function void of further structure. and processes included within the hardware modules.

The invention claimed is:

1. A system for stimulating a dorsal root ganglion of a patient, comprising:
   a elongate flexible implantable stimulation lead comprising a proximal end adapted to receive stimulation pulses from an implantable pulse generator, and a distal end adapted to apply the stimulation pulses to the dorsal root ganglion of the patient, wherein the distal end comprises at least one electrode; and
   an anchor, comprising:
      a first disk and a second disk, wherein each disk is configured to transition between a collapsed configuration and deployed configuration;
      the first disk and the second disk each having a central channel configured to surround the stimulation lead, the central channel configured to allow the anchor to be advanced along the stimulation lead from the proximal end toward the distal end while in the collapsed configuration, and the central channel of each disk configured to grip onto the stimulation lead when the disk is in the deployed configuration so that the disk does not move from a deployed position on the stimulation lead.

2. The system of claim 1, wherein the first disk and the second disk are configured to independently transition from the collapsed configuration and the expanded configuration.

3. The system of claim 1, further comprising:
   a connector attached between the first disk and the second disk and configured to keep the first disk and the second disk in a spaced relationship.

4. The system of claim 1, wherein the first disk and the second disk are configured to be deployed on opposite sides of an anatomical structure with the first disk on the distal side of the structure and the second disk on the proximal side of the structure.

5. The system of claim 4, wherein the anatomical structure is a foraminal ligament.

6. The system of claim 1, wherein the first disk and the second disk of the anchor each comprise a layer of tubular metal fabric having a plurality of braided metal strands, the tubular metal fabric having a preset expanded configuration corresponding to the deployed configuration.

7. The system of claim 1, further comprising an implantable pulse generator configured to provide electrical stimulation to a target dorsal root ganglion using one or more electrodes of the stimulation lead.

8. A system for stimulating a dorsal root ganglion of a patient, comprising:
   a stimulation lead comprising a proximal end adapted to receive stimulation pulses from an implantable pulse generator and a distal end adapted to apply the stimulation pulses to the dorsal root ganglion of the patient, wherein the distal end comprises at least one electrode; and
   an anchor, comprising:
      a first disk configured to move between a collapsed shape and an expanded shape, the first disk having a central opening configured to allow passage of the stimulation lead when the first disk is in the collapsed shape, the central opening configured to grip the stimulation lead in the expanded shape.

9. The system of claim 8, wherein the anchor further comprises:
a second disk configured to move between a collapsed shape and an expanded shape, the second disk having a central opening configured to allow passage of the stimulation lead when the second disk is in the collapsed shape, the central opening configured to grip the stimulation lead in the expanded shape, wherein the first disk is positioned closer to the distal end of the stimulation than the second disk.

10. The system of claim 9, wherein central openings of the first disk and the second disk are configured to grip onto the stimulation lead in the expanded configuration so that each disk does not move from their respective deployed positions on the stimulation lead.

11. The system of claim 10, wherein the first disk and the second disk are configured to be located on opposite sides of a ligament in their respective deployed positions.

12. The system of claim 11, wherein the first disk and the second disk each comprise a metal fabric having a plurality of braided metal strands, the metal fabric having a preset deployed configuration corresponding to the expanded shape of the respective disk, and
wherein the first disk and the second disk lock the stimulation lead in a fixed position relative to the ligament when in their respective deployed positions.

13. The system of claim 9, further comprising:
an anchor deployment tool having a hollow central opening, wherein the first disk and the second disk are located within the central opening while in the collapsed shape.

14. The system of claim 13, wherein the first disk and the second disk are configured to be moved by the anchor deployment tool along the stimulation lead.

15. The system of claim 9, wherein the first disk and the second disk are coupled by a central connector configured to keep the first disk a preset distance from the second disk.

16. The system of claim 8, wherein central opening of the first disk is configured to grip onto the stimulation lead in the expanded configuration so that the disk does not move from a deployed position on the stimulation lead.

17. The system of claim 8, further comprising:
an anchor deployment tool having a hollow central opening, wherein the first disk is located within the central opening while in the collapsed shape.

18. The system of claim 17, wherein the first disk is configured to be moved by the anchor deployment tool along the stimulation lead.

19. The system of claim 8, wherein the first disk comprises a metal fabric having a plurality of braided metal strands, the metal fabric having a preset deployed configuration corresponding to the expanded shape of the first disk.

* * * * *